US008570369B2

(12) United States Patent
Morita

(10) Patent No.: US 8,570,369 B2
(45) Date of Patent: Oct. 29, 2013

(54) IMAGE PROCESSING DEVICE, COMPUTER-READABLE STORAGE MEDIUM, AND IMAGE PROCESSING METHOD

(75) Inventor: Yasunori Morita, Hachioji (JP)

(73) Assignee: Olympus Corporation, Tokyo (JP)

( * ) Notice: Subject to any disclaimer, the term of this patent is extended or adjusted under 35 U.S.C. 154(b) by 568 days.

(21) Appl. No.: 12/731,224

(22) Filed: Mar. 25, 2010

(65) Prior Publication Data

US 2010/0245551 A1  Sep. 30, 2010

(30) Foreign Application Priority Data

Mar. 26, 2009 (JP) ................................. 2009-077565

(51) Int. Cl.
G01J 3/10 (2006.01)
G01J 3/02 (2006.01)
G01N 23/223 (2006.01)

(52) U.S. Cl.
USPC ................................ 348/68; 348/65; 348/345

(58) Field of Classification Search
None
See application file for complete search history.

(56) References Cited

U.S. PATENT DOCUMENTS 6,388,702 B1 * 5/2002 Konomura et al. ............ 348/74
6,790,174 B2 * 9/2004 Kaneko et al. ................ 600/118
7,704,206 B2 * 4/2010 Suzuki et al. ................. 600/178
7,903,846 B2 * 3/2011 Fisher ........................... 382/124
8,055,329 B2 * 11/2011 Kimchy et al. ............... 600/436
8,167,794 B2 * 5/2012 Matsumoto et al. .......... 600/160
2008/0239070 A1 * 10/2008 Westwick et al. .............. 348/68

FOREIGN PATENT DOCUMENTS

| JP | 03-032635 A | 2/1991 |
| JP | 2001-046331 A | 2/2001 |
| JP | 2002-336187 | 11/2002 |
| JP | 2008-183349 A | 8/2008 |

OTHER PUBLICATIONS

Japanese Official Action dated Jul. 16, 2013 received in related application JP 2009-077565 together with an English language translation.

* cited by examiner

Primary Examiner — Gims Philippe
Assistant Examiner — Reza Aghevli
(74) Attorney, Agent, or Firm — Scully, Scott, Murphy & Presser, PC

(57) ABSTRACT

A reflected light image of an observed region and a fluorescent light image of the observed region based on fluorescent light that is generated from the observed region are acquired. The variation component of the acquired latest reflected light image is detected on the basis of the latest reflected light image and an old reflected light image. A correction process is performed on the luminance value of the latest reflected light image taking the variation component into account. A normalization process is performed on the luminance value of the fluorescent light image using the luminance value of the reflected light image after the correction process, which sharpens the image of the region in the observed region from which the fluorescent light is generated.

10 Claims, 11 Drawing Sheets

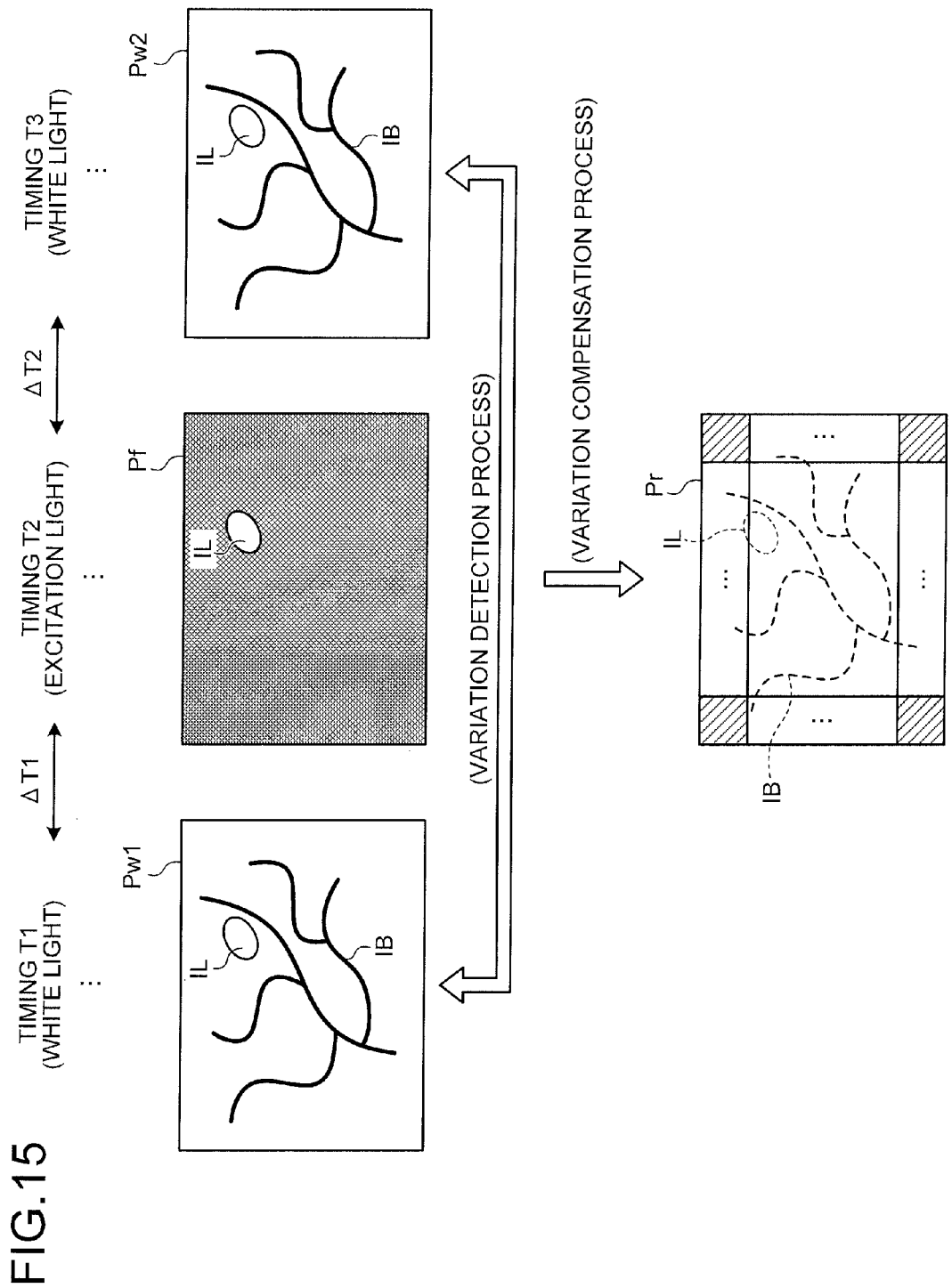

IMAGE PROCESSING DEVICE, COMPUTER-READABLE STORAGE MEDIUM, AND IMAGE PROCESSING METHOD

CROSS-REFERENCE TO RELATED APPLICATIONS

This application is based upon and claims the benefit of priority from Japanese Patent Application No. 2009-077565, filed on Mar. 26, 2009, the entire contents of which are incorporated herein by reference.

BACKGROUND OF THE INVENTION

1. Field of the Invention

The present invention relates to an image processing device, a computer-readable storage medium, and an image processing method and particularly relates to an image processing device, a computer-readable storage medium, and an image processing method for processing a fluorescent light image based on the fluorescent light from an object.

2. Description of the Related Art

Endoscopes are used in the medical field to observe the internal organs of a subject. An elongated and flexible insertion unit of an endoscope is inserted into the body cavity of a subject, such as a patient. White light is applied to body tissue in the body cavity via the inserted flexible insertion unit. By receiving the light reflected from the body tissue with an imaging unit in the flexible insertion unit, a white light image of the body tissue is captured. The white light image of the body tissue is displayed on a display unit of the endoscope. A user, such as a doctor, observes the interior of the body cavity of the subject using the white light image of the body tissue that is displayed on the display unit of the endoscope.

In the field of endoscopy, endoscopes have also been used recently that allow fluorescence observation of an observed region, such as body tissue in the body cavity. A fluorescence-observation endoscope applies excitation light to body tissue in the body cavity via a flexible insertion unit that is inserted into the body cavity and captures a fluorescent light image of the body tissue by receiving, with its imaging unit in the flexible insertion unit, light of autofluorescence or drug fluorescence that is generated from the body tissue due to the application of excitation light. The fluorescent light image of the body tissue that is captured as described above is displayed on the display unit of the endoscope and is observed by a user, such as a doctor. There are also apparatuses that acquire a normalization image using light emitted from an observed region, such as body tissue, due to the application of light on the observed region, and that performs division regarding a fluorescent light image of the observed region using the normalization image in order to generate a normalized fluorescent light image (see, Japanese Laid-open Patent Publication No. 2002-336187).

The luminance value of each pixel of the normalization image decreases with an increase (lengthening) in imaging distance between the observed region and the imaging unit and increases with a decrease (shortening) in the imaging distance between the observed region and the imaging unit.

SUMMARY OF THE INVENTION

An image processing device according to an aspect of the present invention includes a reflected light image acquiring unit that acquires a reflected light image of an observed region, the reflected light image being obtained from light reflected from the observed region; a fluorescent light image acquiring unit that acquires a fluorescent light image of the observed region, the fluorescent light image being obtained from fluorescent light that is generated from the observed region by excitation light; a variation detecting unit that detects a variation component of the reflected light image on the basis of an old reflected light image of the observed region and the reflected light image, the old reflected light image and the reflected light image being acquired by the reflected light image acquiring unit; a correction process unit that performs a correction process on a luminance value of the reflected light image, taking the variation component into account; and a normalization process unit that performs a normalization process on a luminance value of the fluorescent light image, using the luminance value of the reflected light image on which the correction process is performed by the correction process unit.

A computer-readable storage medium according to another aspect of the present invention stores therein an image processing program that contains instructions. The instructions cause a computer to perform: acquiring a reflected light image of an observed region and a fluorescent light image of the observed region, the reflected light image being obtained from light reflected from the observed region, and the fluorescent light image being obtained from fluorescent light that is generated by excitation light; detecting a variation component of the reflected light image; performing a correction process on a luminance value of the reflected light image taking the variation component into account; and performing a normalization process on a luminance value of the fluorescent light image using the luminance value of the reflected light image after the correction process.

An image processing method according to still another aspect of the present invention includes acquiring a reflected light image of an observed region and a fluorescent light image of the observed region, the reflected light image being obtained from light reflected from the observed region, and the fluorescent light image being obtained from on fluorescent light that is generated by excitation light; detecting a variation component of the reflected light image; performing a correction process on a luminance value of the reflected light image taking the variation component into account; and performing a normalization process on a luminance value of the fluorescent light image using the luminance value of the reflected light image after the correction process.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 15 is a schematic diagram for specifically explaining operations of the image processing device according to the second embodiment of the present invention.

DETAILED DESCRIPTION OF THE PREFERRED EMBODIMENTS

Image processing devices, computer-readable storage media, and image processing methods according to embodiments of the present invention are explanation in detail below with reference to the accompanying drawings.

First Embodiment

Figure 1:
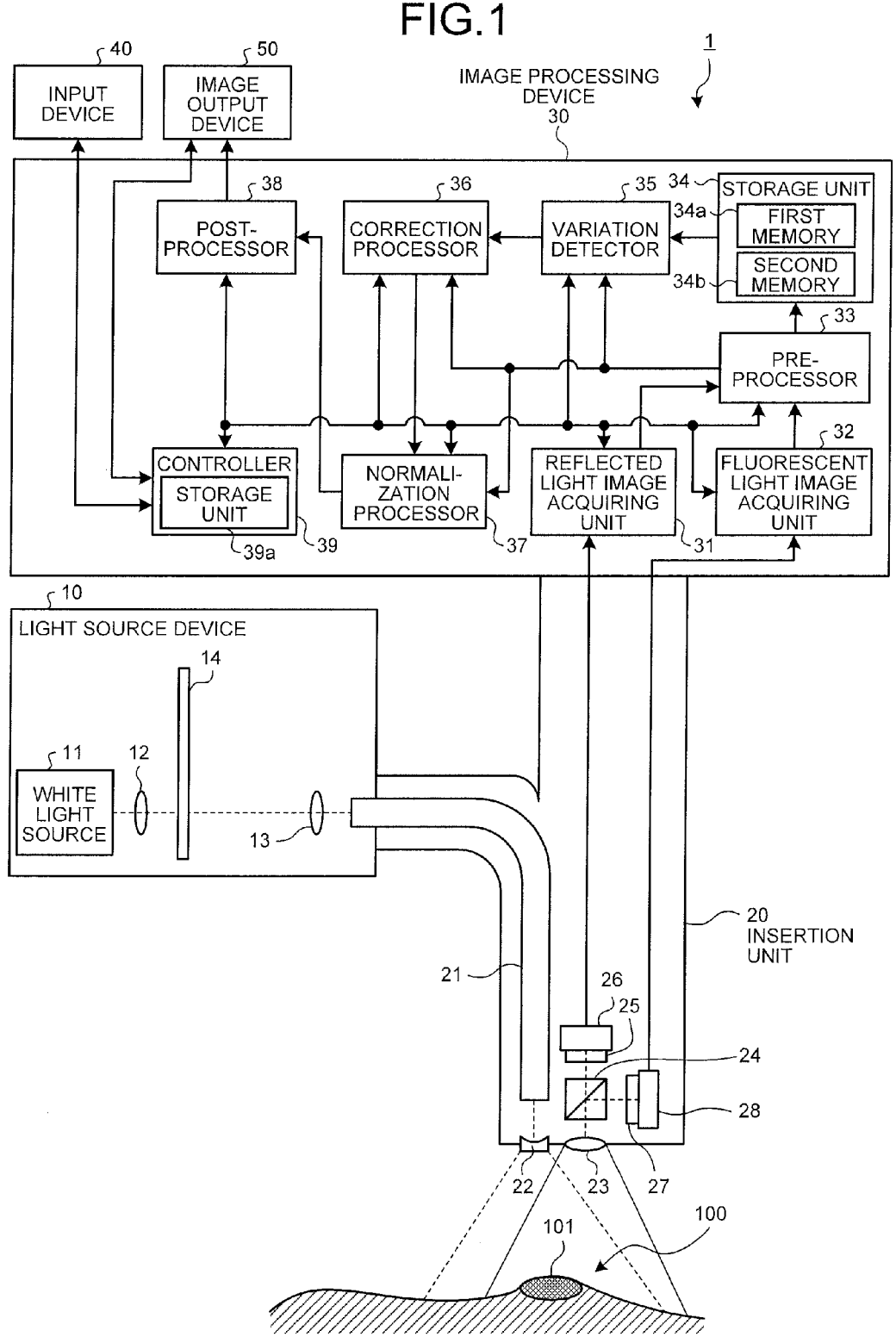
FIG. 1 is a block diagram schematically representing an example of a configuration of an endoscope according to a first embodiment of the present invention.

FIG. 1 is a block diagram schematically representing an example of configuration of an endoscope according to a first embodiment of the present invention. As represented in FIG. 1, an endoscope 1 according to the first embodiment includes a light source device 10 that applies light to an observed region 100 in the interior of a subject, such as a patient; and an elongated insertion unit 20 that is inserted to the body cavity of the subject. The endoscope 1 further includes an image processing device 30 that processes an image of the observed region 100; an input device 40 that inputs various types of information to the image processing device 30; and an image output device 50 that outputs image information that is processed by the image processing device 30.

The light source device 10 functions as a light source unit that applies excitation light that excites a fluorescent agent and white light, which is an example of illuminating light, to the observed region 100. Specifically, the light source device 10 includes a white light source 11; a collimating lens 12 that causes the light emitted from the white light source 11 to be approximately parallel light; a condenser lens 13 that concentrates the collimated light; and a filter 14 that allows light in a predetermined wavelength band to pass through.

The white light source 11 is achieved with a light source that can emit white light of a broadband covering the wavelength band of excitation light that excites the fluorescent agent. The white light source 11 emits a broadband white light in a wavelength band, for example, of 400 to 740 nm on the basis of an operation on a switch (not shown) of the light source device 10. Specifically, the white light that is emitted by the white light source 11 contains color lights of a blue component (B), a green component (G), and a red component (R), and further contains excitation light in a wavelength band of 680 to 740 nm that excites a fluorescent agent, for example, represented by Cy7, accumulated on a lesion 101, such as a tumor. The excitation light from the white light source 11 has a characteristic of exciting the fluorescent agent accumulated on the lesion 101 in order to cause the fluorescent agent to emit fluorescent light in a wavelength band, for example, of 760 to 850 nm excluding the wavelength band of visible light.

The collimating lens 12 is arranged in the optical path of the white light that is emitted from the white light source 11, and cases the white light from the white light source 11 to be approximately parallel light. The light that is collimated by the collimating lens 12 passes through the filter 14, and then is concentrated by the condenser lens 13. The light that is concentrated by the condenser lens 13 is applied via the insertion unit 20 to the observed region 100 in the subject.

Figure 2:
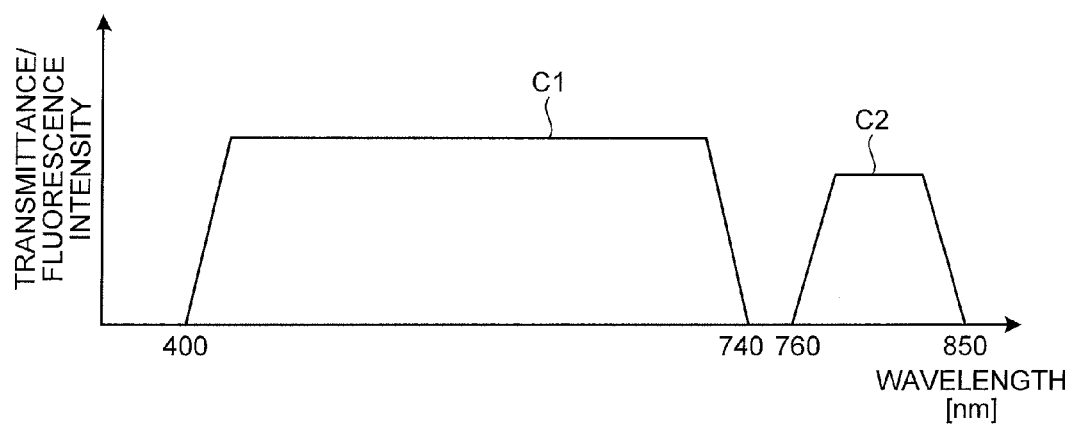
FIG. 2 is a schematic diagram representing an example of transmittance properties of a filter of a light source device according to the first embodiment of the present invention.

The filter 14 extracts light in a predetermined wavelength band out of the white light that is emitted by the white light source 11. FIG. 2 is a schematic diagram representing an example of transmittance properties of the filter of the light source device according to the first embodiment of the present invention. FIG. 2 also illustrates the intensity properties of fluorescent light that is generated due to the excitation light that is extracted by the filter 14 of the light source device 10. The filter 14 has transmittance properties that allow the white light in the wavelength band of 400 to 740 nm to pass through as represented by the correlation line C1 of wavelength with respect to transmittance represented in FIG. 2. The filter 14 extracts the white light in the wavelength band of 400 to 740 nm from the light emitted from the white light source 11 and allows the extracted white light to pass through as the illuminating light to the observed region 100.

The white light that is extracted by the filter 14 contains the excitation light in the wavelength band of 680 to 740 nm, which excites the fluorescent agent (for example, Cy7) accumulated on the lesion 101 in the observed region 100. In other words, the filter 14 allows the white light of the broadband covering the wavelength band of excitation light to pass through. The excitation light in the wavelength band of 680 to 740 nm that passes through the filter 14 causes generation of fluorescent light in the wavelength band of 760 to 850 nm as represented by the correlation line C2 of wavelength with respect to transmittance represented in FIG. 2.

The insertion unit 20 is an elongated flexible structure that can be inserted to the body cavity of the subject, and can be curved in a desired direction on the basis of the operation of an operating unit (not shown) of the endoscope 1. As represented in FIG. 1, the base side of the insertion unit 20 is connected to the light source device 10 and the image processing device 30, and includes a light guide fiber 21 that guides the light emitted from the light source device 10 to the tip portion side; and a lens 22 that diffuses the light that is guided by the light guide fiber 21. The insertion unit 20 further includes an objective lens 23 that concentrates the reflected light or the fluorescent light from the observed region 100; a dichroic mirror 24 that reflects to different directions the concentrated light from the observed region 100; and a reflected light imaging unit 26 that captures a reflected light image based on the reflected light from the observed region 100; and a fluorescent light imaging unit 28 that captures a fluorescent light image based on the fluorescent light from the observed region 100. The reflected light imaging unit 26 includes a color filter group 25 consisting of a plurality of color filters with different spectral properties. The fluorescent light imaging unit 28 includes a barrier filter 27 that allows the fluorescent light from the observed region 100 to pass thorough and that cuts off the excitation light.

The light guide fiber 21 is achieved with optical fibers. The light guide fiber 21 propagates the broadband white light that is emitted by the light source device 10, i.e., the white light covering the wavelength band of excitation light, to the tip portion of the insertion unit 20. The broadband white light from the light source device 10 that is guided by the light guide fiber 21 is diffused by the lens 22 and then applied to the observed region 100 in the subject.

The white light from the light source device 10 that is applied to the observed region 100 illuminates the observed region 100 and is reflected on the observed region 100. When the lesion 101 exists in the observed region 100 where the fluorescent agent is accumulated previously, the excitation light contained in the white light that is applied to the observed region 100 excites the fluorescent agent on the lesion 101 in order to cause generation of a fluorescent light in the wavelength band of 760 to 850 nm.

The objective lens 23 concentrates the reflected light and the fluorescent light from the observed region 100. Specifically, when the white light from the light source device 10 is applied to the observed region 100, the objective lens 23 concentrates the reflected white light and excitation light that are reflected on the observed region 100 and the fluorescent light that is generated from the observed region 100 (specifically, the lesion 101).

The dichroic mirror 24 reflects the light from the observed region 100, which passes through the objective lens 23, to the reflected light imaging unit 26 and the fluorescent light imaging unit 28. Specifically, the dichroic mirror 24 reflects the light in the wavelength band less than 680 nm out of the light from the observed region 100, which is concentrated by the objective lens 23, i.e., the white light reflected from the observed region 100 (for example, the white light of 400 to 680 nm), to the optical path of the reflected light imaging unit 26. The dichroic mirror 24 also has a function of completely reflecting the light in the wavelength band of 680 nm or more and reflects, to the optical path of the fluorescent light imaging unit 28, the fluorescent light that is generated from the observed region 100 and the excitation light that is reflected from the observed region 100. The light from the observed region 100 that is reflected to the fluorescent light imaging unit 28 by the dichroic mirror 24 contains, for example, the excitation light of 680 to 740 nm and the fluorescent light of 760 to 850 nm.

Figure 3:
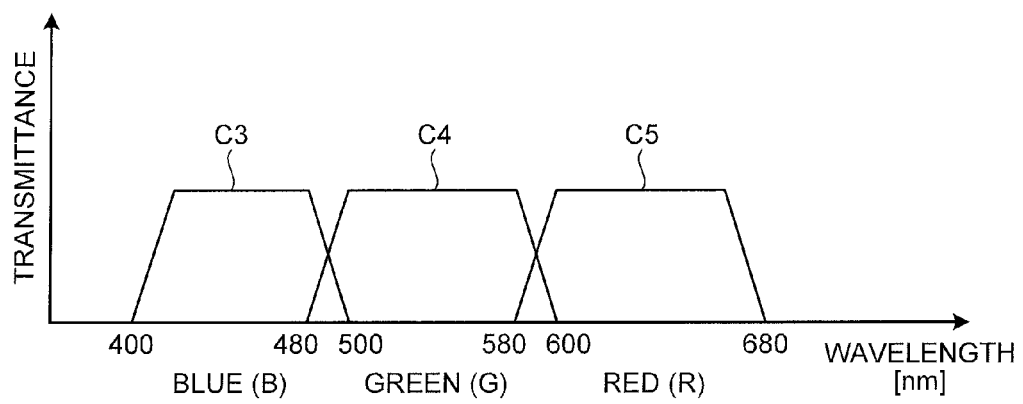
FIG. 3 is a schematic diagram representing an example of transmittance properties of a color filter group in the endoscope represented in FIG. 1.

The color filter group 25 consists of the color filters with different spectral properties. The color filter group 25 separates the white light from the observed region 100 to lights of respective spectrums with respect to each pixel of the reflected light imaging unit 26, and allows the lights of the respective color components to pass through to each pixel of the reflected light imaging unit 26. FIG. 3 is a schematic diagram representing an example of transmittance properties of the color filter group. The color filter group 25 is a mosaic primary color filter that includes a plurality of blue optical filters that are color filters that allow blue light (B) to pass through, a plurality of green light filters that are color filters that allow a green light (G) to pass through, and a plurality of red light filters that are color filters that allow a red light (R) to pass through. In the color filter group 25, the blue color filter has transmittance properties that allow light in the wavelength band of 400 to 500 nm to pass through as represented by the correlation line C3 of wavelength with respect to transmittance shown in FIG. 3. The green color filter has transmittance properties that allow light in the wavelength band of 480 to 600 nm to pass through as represented by the correlation line C4 of wavelength with respect to transmittance shown in FIG. 3. The red color filter has transmittance properties that allow light in the wavelength band of 580 to 680 nm to pass through as represented by the correlation line C5 of wavelength with respect to transmittance shown in FIG. 3.

The color filter group 25 having such a configuration extracts, with the blue light filter, the blue light from the white light from the observed region 100, which is reflected by the dichroic mirror 24 to the optical path of the reflected light imaging unit 26, extracts the green light with the green light filter, and extracts the red light with the red light filter. Each blue light filter of the color filter group 25 allows the blue component of the white light to pass through toward each pixel of the reflected light imaging unit 26, which pixel corresponds to blue. Each green light filter of the color filter group 25 allows the green component of the white light to pass through toward each pixel of the reflected light imaging unit 26, which pixel corresponding to green. Each red light filter of the color filter group 25 allows the red component of the white light to pass through toward each pixel of the reflected light imaging unit 26, which pixel corresponding to red.

The reflected light imaging unit 26 is used to capture a reflected light image based on the reflected light from the observed region 100. The reflected light imaging unit 26 is achieved with a Bayer color imaging device in which color filters with different spectral properties are arranged on the respective pixels in the light receiving surface. Specifically, the reflected light imaging unit 26 includes an infrared light cut filter (not shown) that removes infrared light and the color filter group 25 both of which are arranged on the light receiving surface. The reflected light imaging unit 26 receives, via the color filter group 25, the reflected light from the observed region 100, which is reflected by the dichroic mirror 24 to the optical path of the reflected light imaging unit 26 (for example, the white light that is reflected from the observed region 100 when the white light from the light source device 10 is applied to the observed region 100). Accordingly, the reflected light imaging unit 26 captures a white light image that is an example of the reflected light image of the observed region 100. In this case, the reflected light imaging unit 26 performs a photoelectric conversion process on each reflected light of each color components, into which the white light from the observed region 100 is separated by the color filter group 25, depending on each pixel in order to generate a video signal of each color component that constitutes the white light image of the observed region 100. Each time the reflected light imaging unit 26 captures a white light image of the observed region 100, the reflected light imaging unit 26 sequentially transmits each video signal of the white light image of the observed region 100 to the image processing device 30.

Figure 4:
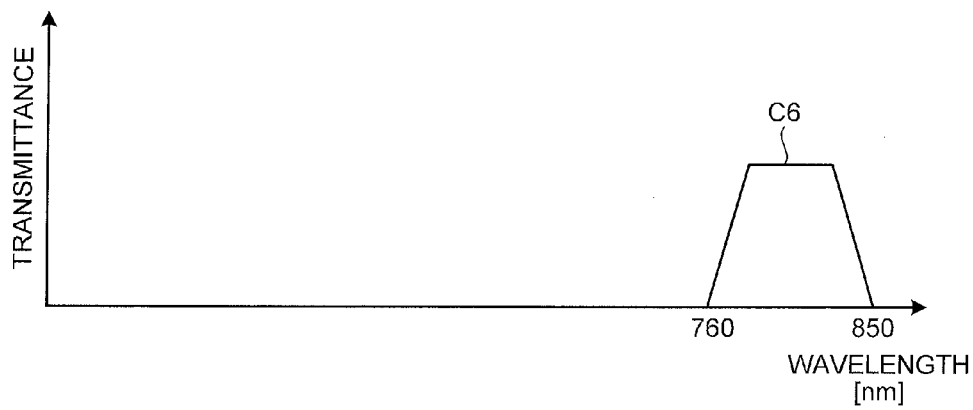
FIG. 4 is a schematic diagram representing an example of transmittance properties of a barrier filter according to the first embodiment of the present invention.

The barrier filter 27 is achieved with an excitation light cut filter. The barrier filter 27 cuts off the excitation light that is contained in the light from the observed region 100, which is reflected by the dichroic mirror 24 to the optical path of the fluorescent light imaging unit 28. FIG. 4 is a schematic diagram representing an example of transmittance properties of the barrier filter according to the first embodiment. The barrier filter 27 has transmittance properties that allow light in the wavelength band of 760 to 850 nm to pass through as represented by the correlation line C6 of wavelength with respect to transmittance. The barrier filter 27 cuts off the excitation light that is reflected from the observed region 100 (for example, the excitation light in the wavelength band of 680 to 740 nm) out of the light that is reflected by the dichroic mirror 24 to the optical path of the fluorescent light imaging unit 28. The barrier filter 27 also allows the fluorescent light (for example, 760 to 850 nm) not covering the wavelength band of visible light from the observed region 100.

The fluorescent light imaging unit 28 is used to capture a fluorescent light image based on fluorescent light from the observed region 100. Specifically, the fluorescent light imaging unit 28 is achieved with a monochrome imaging device having sensitivity, for example, higher than that of the reflected light imaging unit 26. On the light receiving surface of the fluorescent light imaging unit 28, the barrier filter 27 is arranged. As in the case of the reflected light imaging unit 26, when the white light from the light source device 10 is applied to the observed region 100, the fluorescent light imaging unit 28 receives the fluorescent light passes through the barrier filter 27 out of the excitation light and the fluorescent light from the observed region 100, which is reflected by the dichroic mirror 24 to the optical path of the fluorescent light imaging unit 28. Accordingly, the fluorescent light imaging unit 28 captures a fluorescent light image of the observed region 100. In this case, the fluorescent light imaging unit 28 performs the photoelectric conversion process on the fluorescent light from the observed region 100, with respect to each pixel in the light receiving part, in order to generate video signals that constitute the fluorescent light image of the observed region 100. Each time the fluorescent light imaging unit 28 captures a fluorescent light image of the observed region 100, the fluorescent light imaging unit 28 sequentially transmits each video signal of the fluorescent light image of the observed region 100 to the image processing device 30.

In the first embodiment, the reflected light imaging unit 26 captures the white light image of the observed region 100 during a period in which the white light from the light source device 10 is applied to the observed region 100, and the fluorescent light imaging unit 28 captures the fluorescent light image of the observed region 100 during the same period as that in which the white light is applied. In other words, the white light image that is captured by the reflected light imaging unit 26 and the fluorescent light image that is captured by the fluorescent light imaging unit 28 are taken at the same timing and thus the positions of the subject between those images coincide with each other.

The image processing device 30 processes image information on the observed region 100 of which images are captured by the reflected light imaging unit 26 or the fluorescent light imaging unit 28 in order to generate an output image to be output by the image output device 50. Specifically, as represented in FIG. 1, the image processing device 30 includes a reflected light image acquiring unit 31 that acquires the reflected light image of the observed region 100, which is captured by the reflected light imaging unit 26; a fluorescent light image acquiring unit 32 that acquires the fluorescent light image of the observed region 100, which is captured by the fluorescent light imaging unit 28; and a pre-processor 33 that performs predetermined signal processes on the reflected light image and the fluorescent light image of the observed region 100. The image processing device 30 further includes a storage unit 34 that stores the reflected light image after the process by the pre-processor 33; a variation detector 35 that detects a variation component of the reflected light image of the observed region 100; and a correction processor 36 that performs a correction process on the luminance value of the reflected light image of the observed region 100 taking the detected variation component into account. The image processing device 30 further includes a normalization processor 37 that performs a normalization process on the luminance value of the fluorescent light image of the observed region 100 using the luminance value of the reflected light image after the correction process by the correction processor 36; a post-processor 38 that performs predetermined signal processes on the fluorescent light image of the observed region 100 after the normalization process; and a controller 39 that controls each constituent of the image processing device 30.

In the image processing device 30, the reflected light image acquiring unit 31 and the fluorescent light image acquiring unit 32 are connected to the pre-processor 33. The pre-processor 33 is connected to the storage unit 34, the variation detector 35, the correction processor 36, and the normalization processor 37. The storage unit 34 is connected to the variation detector 35, and the variation detector 35 is connected to the correction processor 36. The correction processor 36 is connected to the normalization processor 37, and the normalization processor 37 is connected to the post-processor 38. The post-processor 38 is connected to the image output device 50 outside the image processing device 30. On the other hand, the controller 39 has bidirectional connection with the reflected light image acquiring unit 31, the fluorescent light image acquiring unit 32, the pre-processor 33, the variation detector 35, the correction processor 36, the normalization processor 37, and the post-processor 38. The controller 39 has bidirectional connection with the input device 40 and the image output device 50 outside the image processing device 30.

The reflected light image acquiring unit 31 acquires the reflected light image based on the reflected light from the observed region 100. Specifically, each time the reflected light imaging unit 26 captures a white light image of the observed region 100, which is an example of a reflected light image, the reflected light image acquiring unit 31 acquires each video signal of the white light image of the observed region 100 from the reflected light imaging unit 26. Each video signal of the white light image is an analog signal, and the analog signals are sequentially output from the reflected light imaging unit 26 to the reflected light image acquiring unit 31 at a predetermined time interval. The reflected light image acquiring unit 31 converts each video signal of the white light image, which is acquired from the reflected light imaging unit 26, from an analog signal to a digital signal, and sequentially transmits each video signal after the digital conversion to the pre-processor 33.

The fluorescent light image acquiring unit 32 acquires the fluorescent light image based on the fluorescent light from the observed region 100. Specifically, each time the fluorescent light imaging unit 28 captures a fluorescent light image of the observed region 100, the fluorescent light image acquiring unit 32 acquires each video signal of the fluorescent light image of the observed region 100 from the fluorescent light imaging unit 28. Each video signal of the fluorescent light image is an analog signal, and the analog signals are sequentially output to the fluorescent light image acquiring unit 32 from the fluorescent light imaging unit 28 at a predetermined time interval. The fluorescent light image acquiring unit 32 converts each video signal of the fluorescent light image, which is acquired from the fluorescent light imaging unit 28, from an analog signal to a digital signal, and sequentially transmits each video signal after the digital conversion to the pre-processor 33.

The pre-processor 33 performs the predetermined signal processes on the reflected light image and the fluorescent light image of the observed region 100. Specifically, the pre-processor 33 acquires each video signal of the white light image after the digital conversion and performs the signal processes, such as an interpolation process, a white balance process, and a noise reduction process on each video signal of the acquired white light image. The pre-processor 33 acquires each video signal of the fluorescent light image after the digital conversion and performs the similar signal processes on each video signal of the acquired fluorescent light image. The pre-processor 33 further performs a calibration process, regarding the spatial position, angle, and size, on each video signal of the white light image and the fluorescent light image of the observed region 100 in order to calibrate the white light image and the fluorescent light image to m×n-pixel image information (both m and n are integers) of each video signal. The pre-processor 33 transmits the processed white light image (m×n-pixel white light image) to the storage unit 34, the variation detector 35, and the correction processor 36. In this case, the pre-processor 33 transmits each video signal of the white light image being processed to the variation detector 35 and the correction processor 36, and further stores in the storage unit 34 each video signal of the white light image being processed. Although the detail is given below, the video signals that are transmitted by the pre-processor 33 are sequentially stored in the storage unit 34. The storage unit 34 according to the first embodiment includes a first memory 34a and a second memory 34b as represented in FIG. 1. The first memory 34a stores each video signal of the latest white light image and the second memory 34b stores each video signal of an old white light image that is transferred from the first memory 34a. Specifically, when each video signal of the latest white light image being processed is input to the first memory 34a, each video signal of the white light image that already exists in the first memory 34a is transferred to the second memory 34b and stored in the second memory 34b as each video signal of the old white light image. Each video signal of the old white light image that is stored in the second memory 34b is then transmitted to the variation detector 35. The pre-processor 33 also transmits the processed fluorescent light image (m×n-pixel fluorescent light image) to the normalization processor 37.

The calibration value of the calibration process that is performed by the pre-processor 33 is calculated on the basis of the image information that is obtained by capturing a known test pattern. The calibration value may be set previously by the user or may be set in a way that the pre-processor 33 automatically detects corresponding points between the reflected light image, which is captured by the reflected light imaging unit 26, and the fluorescent light image, which is captured by the fluorescent light imaging unit 28, each time the calibration process is performed and the pre-processor 33 sets the calibration value on the bases of the result of the detection.

The storage unit 34 stores the reflected light image after the processing by the pre-processor 33. Specifically, the storage unit 34 includes the first memory 34a and the second memory 34b as described above. The storage unit 34 acquires, from the pre-processor 33, the white light image of the observed region 100 that is calibrated by the pre-processor 33 to the m×n-pixel image information, and stores the acquired white light image. Each time the storage unit 34 acquires a reflected light image after the processing by the pre-processor 33, the storage unit 34 sequentially updates the existing information in the first memory 34a to the acquired image information as described above. The white light image that is stored in the second memory 34b of the storage unit 34 is the white light image older than (for example, one frame prior to) the white light image to which the correction process is to be performed by the correction processor 36. The old white light image in the second memory 34b is appropriately read by the variation detector 35.

The variation detector 35 detects the variation component of the current reflected light image on the basis of the current reflected light image of the observed region 100, which is acquired by the reflected light image acquiring unit 31, and the old reflected light image of the observed region 100. Specifically, the variation detector 35 acquires, from the pre-processor 33, the white light image of the observed region 100 (the white light image to be processed) that is processed by the pre-processor 33. In addition, the variation detector 35 reads from the storage unit 34 the white light image (the old-white light image) of the observed region 100 that was taken prior to the white light image to be processed. The variation detector 35 detects the variation component of the white light image to be processed on the basis of the white light image to be processed and the old white light image, for example, with the block matching method. The variation detector 35 generates, as the result of detecting the variation component of the white light image to be processed, a variation component map that contains the information on the detected variation component with respect to each set of pixel coordinates of the white light image to be processed.

The relation between magnitudes in variation component that is detected by the variation detector 35 corresponds to the relation between magnitudes in imaging distance to the subject. In other words, the imaging distance to the subject of each pixel in the white light image to be processed decreases with an increase in variation component and increases with a decrease in variation component.

The variation detector 35 has a function for performing a filtering process on the white light image to be processed. Specifically, the variation detector 35 performs a process for comparing the luminance value of a pixel of interest in the white light image to be processed with the luminance value of pixels neighboring to the pixel of interest with respect to each pixel, and determines whether a positive reflected light pixel is contained in the white light image to be processed on the basis of the result of the luminance comparison process with respect to each pixel. The positive reflected light pixel is a pixel that receives the positive reflected light from the object, such as the observed region 100, and has a remarkably high luminance value compared to that of the neighboring pixels. In the luminance comparison process, when the difference between the luminance value of an arbitrary pixel of interest and that of pixels neighboring to the pixel of interest is a predetermined threshold or higher, the variation detector 35 determines that the white light image to be processed contains a positive-reflected light pixel. In this case, the variation detector 35 performs a filtering process for interpolating the pixel of interest of which luminance difference is the threshold or higher, i.e., the positive reflected light pixel, with the neighboring pixels. Accordingly, the variation detector 35 corrects the luminance value of the positive reflected light pixel to the luminance level of the received-light pixel other than that of the positive reflected light. The variation detector 35 transmits the variation component map of the white light image after the filtering process to the correction processor 36.

The filtering process that is performed by the variation detector 35 may be a median filter process based on a square pixel area of 3×3 pixels or 5×5 pixels or a median filter process based on a rectangular pixel area, for example, of 3×5 pixels. The filtering process that is performed by the variation detector 35 may be a low-pass filter process.

The correction processor 36 corrects the luminance of the reflected light image to be processed taking into account the variation component of the reflected light image, which is detected by the variation detector 35. Specifically, the correction processor 36 acquires the white light image to be processed from the pre-processor 33 and acquires the variation component map of the white light image to be processed from the variation detector 35. The correction processor 36 takes the variation component in the variation component map into account for the luminance value of the white light image to be processed with respect to each corresponding pixel between the acquired white light image to be processed and variation component map. In this manner, the correction processor 36 corrects the luminance of the white light image to be processed according to the variation component of each pixel that varies with an increase or decrease in imaging distance between the object and the reflected light imaging unit 26. In the correction process, the correction processor 36 reduces the luminance of each pixel in the white light image to be processed along with an increase in imaging distance and increases it along with a decrease in imaging distance. Accordingly, regardless of whether there is a positive reflected light pixel, the correction processor 36 generates the white light image of the observed region 100, which is the object, with a luminance distribution that accurately reflects the imaging distance between the observed region 100 and the reflected light imaging unit 26. The correction processor 36 transmits the white light image after the correction process to the normalization processor 37.

The normalization processor 37 corrects, by the normalization process, the luminance value of the fluorescent light image of the observed region 100 that is captured by the fluorescent light imaging unit 28. Specifically, the normalization processor 37 acquires, from the pre-processor 33, the fluorescent light image of the observed region 100 that is processed by the pre-processor 33, and acquires, from the correction processor 36, the white light image of the observed region 100 of which luminance is corrected by the correction processor 36. The normalization processor 37 divides the luminance value of the fluorescent light image by the corrected luminance value of the white light image with respect to each corresponding pixel between the acquired white light image and fluorescent light image of the observed region 100 in order to normalize the luminance value of each pixel of the fluorescent light image. Accordingly, without influence of the positive reflected light from the object, the normalization processor 37 accurately corrects the brightness and darkness (the luminance value) in the fluorescent light image that vary according to the imaging distance between the observed region 100, which is the object, and the fluorescent light imaging unit 28. In the fluorescent light image, on which the normalization process is performed by the normalization processor 37, (hereinafter, "normalized fluorescent light image") the lesion 101 from which the fluorescent light is generated due to application of excitation light is drawn with pixels with relatively high luminance regardless of the imaging distance between the observed region 100 and the fluorescent light imaging unit 28. The normalization processor 37 transmits the normalized fluorescent light image of the observed region 100 to the post-processor 38.

The post-processor 38 performs the predetermined signal processes on the normalized fluorescent light image that is processed by the normalization processor 37. Specifically, the post-processor 38 acquires each video signal of the normalized fluorescent light image of the observed region 100 from the normalization processor 37, and performs the signal processes, such as a gradation conversion process, an enhancement process, and a compression process, on the acquired video signals of the fluorescent light image. The post-processor 38 transmits the normalized fluorescent light image after the signal processes to the image output device 50.

The controller 39 controls each operation of the reflected light image acquiring unit 31, the fluorescent light image acquiring unit 32, the pre-processor 33, the variation detector 35, the correction processor 36, the normalization processor 37, and the post-processor 38, which are constituents of the image processing device 30, and also controls input and output of signals between the constituents. The controller 39 also controls the image output device 50 and the input device 40 that functions as an external interface unit of the image processing device 30.

Specifically, the controller 39 is achieved with a storage unit 39a that stores predetermined process programs including an image processing program, and a computer that executes the process programs in the storage unit 39a. The storage unit 39a is a computer-readable storage medium according to the first embodiment. On the basis of setting information that is input by the input device 40, the controller 39 sets various image-capturing conditions, such as a mode in which a white light image or a fluorescent light image of the observed region 100 is captured, or a gain. The controller 39 controls the start of operation, completion of operation, and operation timing of each constituent of the image processing device 30 on the basis of instruction information that is input by the input device 40.

Specifically, the controller 39 controls the reflected light image acquiring unit 31 such that it sequentially outputs each video signal of the white light image, which is captured by the reflected light imaging unit 26, to the preprocessor 33 after each video signal is converted to a digital signal. The controller 39 controls the pre-processor 33 such that, after the pre-determined processes, the pre-processor 33 transmits the white light image of the observed region 100 to the variation detector 35 and the correction processor 36 and transmits the white light image to the storage unit 34. The controller 39 controls the pre-processor 33 such that, after the predetermined processes, the pre-processor 33 transmits the fluorescent light image of the observed region 100 to the normalization processor 37.

The controller 39 controls the variation detection process on the white light image to be processed, which is performed by the variation detector 35; the luminance correction process on the white light image, which is performed by the correction processor 36; the normalization process on the fluorescent light image, which is performed by the normalization processor 37; and the signal processes on the fluorescent light image, which are performed by the post-processor 38. The controller 39 also controls the post-processor 38 such that it transmits each video signal of the normalized fluorescent light image of the observed region 100 to the image output device 50 on the basis of the instruction information that is input by the input device 40, and controls the image output device 50 such that it displays and outputs the normalized fluorescent light image.

The input device 40 functions as the external interface unit of the image processing device 30. The input device 40 is achieved with input devices, for example, illustrated as a keyboard and a mouse. The input device 40 inputs various types of information to the controller 39 of the image processing device 30 in response to the input operation by the user, such as a doctor or a nurse. The various types of information that are input by the input device 40 to the controller 39 include, for example, instruction information for instructing the controller 39 to start or complete an operation of the image processing device 30 and information for setting the mode in which a white light image or a fluorescent light image of the observed region 100 is captured.

The input device 40 may include a power supply switch that switches on or switches off the image processing device 30, may include a shutter button for starting the image capturing operation, or may include a mode switching button for switching between various modes including the image capturing mode. In this case, the controller 39 controls the image capturing operation of the reflected light imaging unit 26 and the fluorescent light imaging unit 28 in response to the input operation of the shutter button of the input device 40.

The image output device 50 outputs image information that is processed by the image processing device 30. Specifically, the image output device 50 is achieved with a desired display, such as a CRT display or a liquid crystal display. The image output device 50 acquires each video signal of the normalized fluorescent light image of the observed region 100 after the signal processes that are performed by the post-processor 38 of the image processing device 30. The image output device 50 displays the normalized fluorescent light image of the observed region 100 based on each video signal that is acquired from the post-processor 38.

In addition to the normalized fluorescent light image, the image output device 50 may acquire the white light image of the observed region 100, which is captured at the same timing as that of the normalized fluorescent light image, via the pre-processor 33 and the post-processor 38, and may display the white light image and the normalized fluorescent light image of the observed region 100. In this case, the image output device 50 may display the white light image and the normalized fluorescent light image of the observed region 100 side by side, or may display them such that the white light image of the observed region 100 is superimposed on the normalized fluorescent light image.

Figure 5:
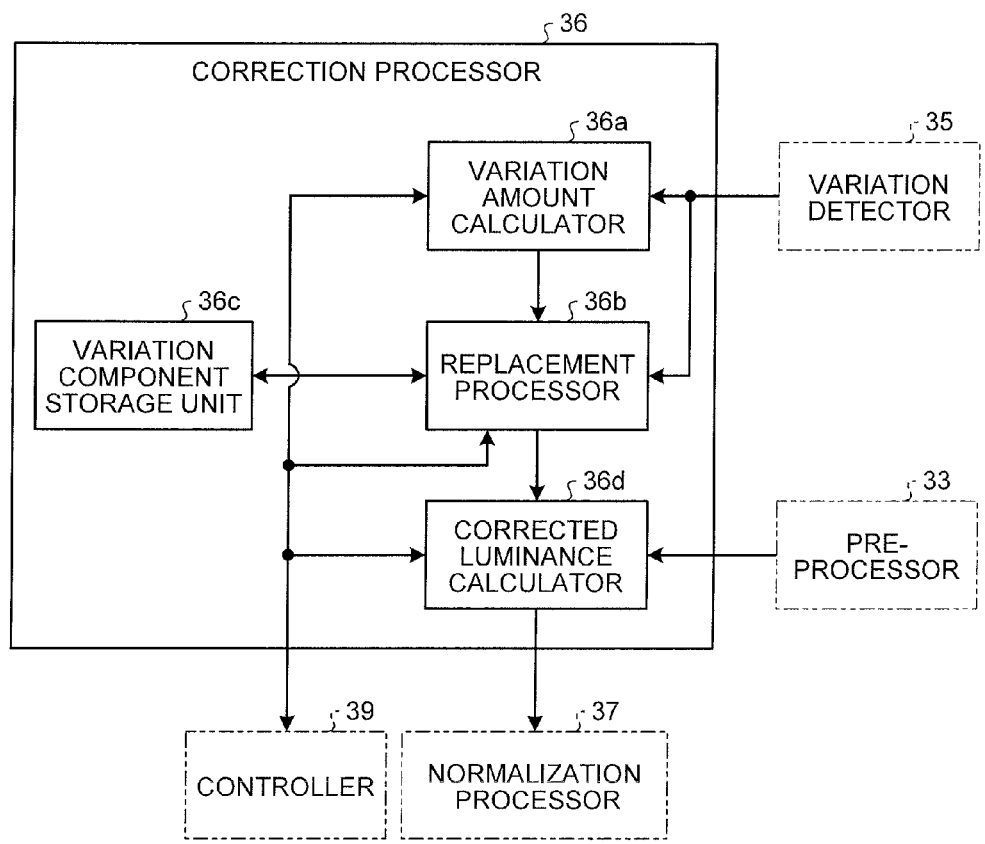
FIG. 5 is a block diagram schematically representing an example of a configuration of a correction processor of an image processing device according to the first embodiment of the present invention.

The correction processor 36 of the image processing device 30 is explained in detail below. FIG. 5 is a block diagram schematically representing an example of a configuration of the correction processor of the image processing device according to the first embodiment of the present invention. As represented in FIG. 5, the correction processor 36 includes a variation amount calculator 36a that calculates the general amount of variation in the white light image to be processed, and a replacement processor 36b that performs a replacement process on the variation component map. The correction processor 36 further includes a variation component storage unit 36c that stores the variation component map of the white light image; and a corrected luminance calculator 36d that calculates a corrected luminance value of the white light image to be processed on the basis of the variation component map.

The variation amount calculator 36a calculates the general amount of the white light image to be processed under the control of the controller 39. Specifically, the variation amount calculator 36a acquires the variation component map of the white light image to be processed, which is detected by the variation detector 35. The variation amount calculator 36a calculates a general amount of the white light image to be processed on the basis of the variation component of each pixel contained in the variation component map, which is acquired from the variation detector 35. Under the control of the controller 39, the variation amount calculator 36a sequentially transmits the general variation amount of the white light image to be processed, which is calculated as described above, to the replacement processor 36b. The variation amount calculator 36a may calculate, as the general variation amount of the white light image to be processed, the average value of variation component of each pixel in the variation component map or may calculate the general value of variation component of each pixel.

The replacement processor 36b appropriately perform the variation component replacement process on the white light image to be processed under the control of the controller 39. Specifically, the replacement processor 36b acquires the variation component map of the white light image to be processed, which is detected by the variation detector 35, and the general variation amount of the white light image to be processed, which is calculated by the variation amount calculator 36a. The replacement processor 36b compares the general variation amount, which is acquired from the variation amount calculator 36a, with a predetermined threshold. When the general variation amount is the threshold or higher, the replacement processor 36b determines that the observed region 100, which is the object in the white light image to be processed, has the predetermined variation or more. In this case, under the control of the controller 39, the replacement processor 36b outputs the variation component map, which is acquired from the variation detector 35, to the corrected luminance calculator 36d and outputs the variation component map to the variation component storage unit 36c as a variation component map that is obtained when the subject has the predetermined variation or more. In contrast, when the general variation amount is lower than the threshold, the replacement processor 36b determines that the object in the white light image to be processed (the observed region 100) does not have the predetermined variation or more. In this case, under the control of the controller 39, the replacement processor 36b replaces the variation component map, which is acquired from the variation detector 35, with the variation component map in the variation component storage unit 36c and outputs the variation component map in the variation component storage unit 36c to the corrected luminance calculator 36d.

The threshold that is previously set in the replacement processor 36b may be a threshold that is set by the controller 39 on the basis of the information that is input by the input device 40, or may be a threshold that is automatically set by the controller 39 on the basis of the focal distance of the objective lens 23.

The variation component storage unit 36c stores the variation component of the white light image that is a white light image of which object has the predetermined variation or more, and that is older than the white light image to be processed. Specifically, the variation component storage unit 36c acquires, from the replacement processor 36b, the variation component map of the white light image to which the replacement processor 36b determines that the object has the predetermined variation or more, i.e., the variation component map that is obtained in the case where the general variation amount calculated by the variation amount calculator 36a is the threshold or higher. The variation component storage unit 36c stores the acquired variation component map. The variation component map that is stored in the variation component storage unit 36c is the variation component map of the white light image older than the subsequent white light image to be processed, and is appropriately read by the replacement processor 36b in the variation component replacement process. Each time the variation component storage unit 36c acquires a variation component map from the replacement processor 36b, the variation component storage unit 36c overwrites the existing variation component map with the acquired latest variation component map to update the variation component map.

The corrected luminance calculator 36d calculates the corrected luminance of the white light image to be processed under the control of the controller 39. Specifically, the corrected luminance calculator 36d acquires the variation component map that is output by the replacement processor 36b and the white light image to be processed, which is processed by the pre-processor 33. The corrected luminance calculator 36d corrects the luminance value of each pixel of the white light image to be processed taking into account the variation component of each pixel contained in the variation component map, which is acquired from the replacement processor 36b. In other words, the corrected luminance calculator 36d calculates a corrected luminance value calculated taking into account the variation component in the variation component map with respect to each corresponding pixel between the white light image to be processed and the variation component map. The corrected luminance calculator 36d transmits the corrected luminance value of each pixel of the white light image to the normalization processor 37 under the control of the controller 39.

Figure 6:
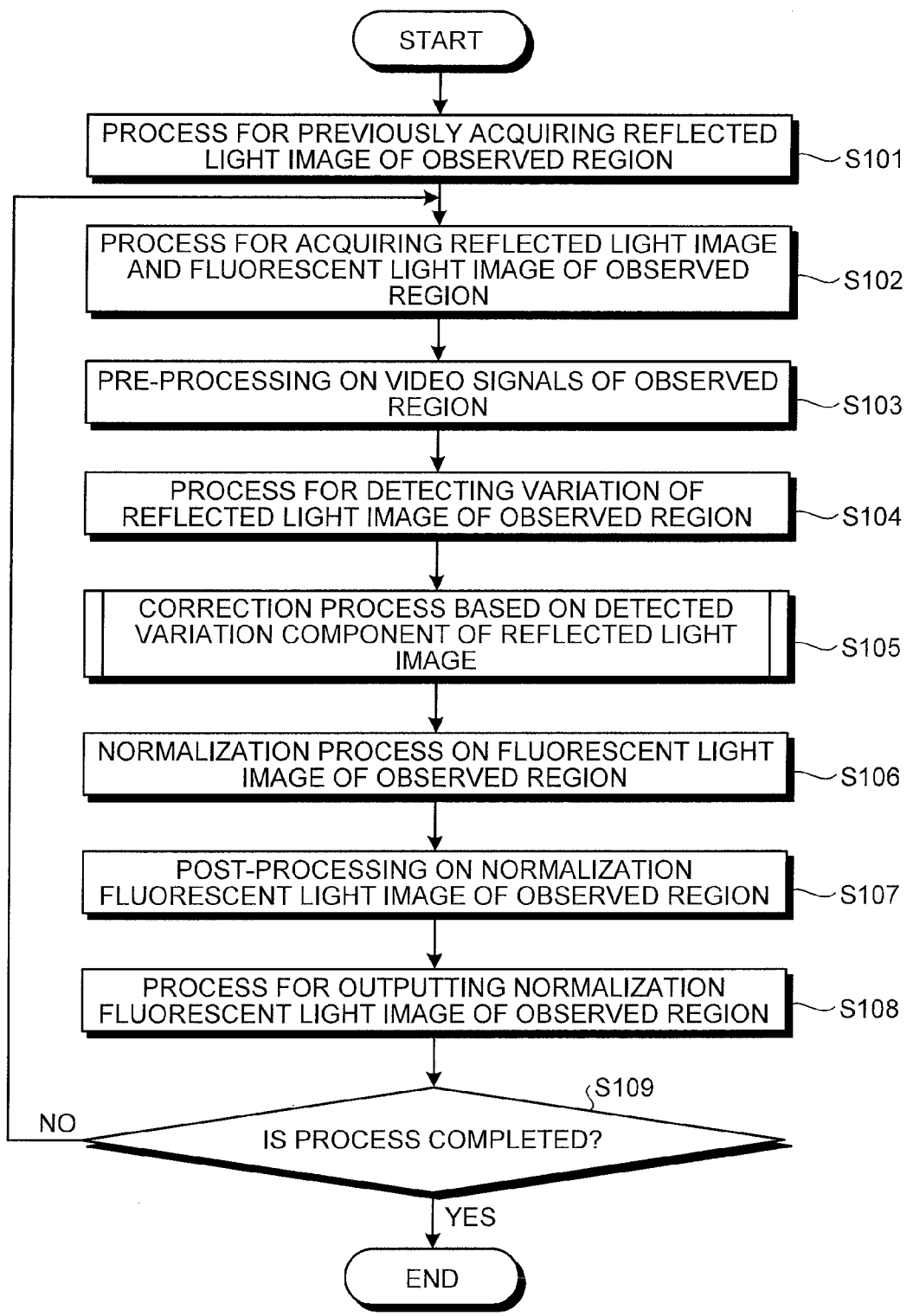
FIG. 6 is a flowchart illustrating a process procedure of the image processing device according to the first embodiment of the present invention.

The operations of the image processing device 30 according to the first embodiment of the present invention are explained below. FIG. 6 is a flowchart illustrating the process procedure of the image processing device according to the first embodiment of the present invention. The image processing device 30 according to the first embodiment performs the process procedure represented in FIG. 6 to cause the image output device 50 to display the normalized fluorescent light image of the observed region 100.

In other words, as represented in FIG. 6, the image processing device 30 previously acquires the reflected light image of the observed region 100 (S101). At step S101, the controller 39 controls the reflected light image acquiring unit 31 and the pre-processor 33 to acquire to previously acquire the white light image of the observed region 100.

Under the control of the controller 39, the reflected light image acquiring unit 31 acquires the white light image of the observed region 100, which is taken by the reflected light imaging unit 26 at the timing at which the white light from the light source device 10 is applied to the observed region 100, converts each video signal of the acquired white light image to a digital signal, and then transmits the video signals to the pre-processor 33. Under the control of the controller 39, the pre-processor 33 performs the signal processes on each video signal of the white light image, which is acquired from the reflected light image acquiring unit 31, and then transmits each video signal of the white image to the storage unit 34. The storage unit 34 stores the white light image of the observed region 100, which is acquired from the pre-processor 33, as the white light image older than the white light image of the observed region 100 to be processed later.

At step S101, the controller 39 may control the fluorescent light image acquiring unit 32 such that it deletes the fluorescent light image of the observed region 100, which is captured by the fluorescent light imaging unit 28 at the same timing as that of the white light image. Alternatively, the controller 39 may control the normalization processor 37 to perform the normalization process on the fluorescent light image, using the white light image of the observed region 100 that is acquired at step S101, and then may control the post-processor 38 and the image output device 50 to display and output the normalized fluorescent light image, on which normalization process is performed by the normalization processor 37.

Subsequently, the image processing device 30 acquires the reflected light image of the observed region 100 to be processed and the fluorescent light image (step S102). At step S102, the controller 39 controls the reflected light image acquiring unit 31 such that it acquires the white light image of the observed region 100, and controls the fluorescent light image acquiring unit 32 such that it acquires the fluorescent light image of the observed region 100.

Under the control of the controller 39, the reflected light image acquiring unit 31 acquires the white light image of the observed region 100, which is captured by the reflected light imaging unit 26 at the timing at which the white light from the light source device 10 is applied to the observed region 100, and converts each video signal of the acquired white light image to a digital signal. The reflected light image acquiring unit 31 transmits the white light image on which the digital conversion is performed to the pre-processor 33. On the other hand, under the control of the controller 39, the fluorescent light image acquiring unit 32 acquires the fluorescent light image of the observed region 100, which is captured by the fluorescent light imaging unit 28 at the same timing as that of the white light image, and converts each video signal of the fluorescent light image to a digital signal. The fluorescent light image acquiring unit 32 transmits the fluorescent light image on which digital conversion is performed to the pre-processor 33.

Subsequently, the image processing device 30 performs the pre-processing on the video signals of the observed region 100, which is acquired at step S102 (step S103). At step S103, the controller 39 controls the pre-processor 33 such that it performs the predetermined signal processes and the calibration process on each image of the observed region 100.

Under the control of the controller 39, the pre-processor 33 performs the signal processes, such as the interpolation process, the white balance process, the noise reduction process, and the calibration process for spatial position, angle, and size, on the white light image of the observed region 100, which is acquired from the reflected light image acquiring unit 31. Accordingly, the pre-processor 33 calibrates the white light image of the observed region 100 to m×n-pixel image information. Under the control of the controller 39, the pre-processor 33 transmits the calibrated white light image of the observed region 100 to the variation detector 35 and the correction processor 36 as the white light image to be processed. Similarly, under the control of the controller 39, the pre-processor 33 performs the signal processes, such as the interpolation process, the white balance process, the noise reduction process, and the calibration process for spatial position, angle, and size, on the fluorescent light image of the observed region 100, which is acquired from the fluorescent light image acquiring unit 32. Accordingly, the pre-processor 33 calibrates the fluorescent light image of the observed region 100 to m×n-pixel image information as in the case of the white light image to be processed. Under the control of the controller 39, the pre-processor 33 transmits the calibrated fluorescent light image of the observed region 100 to the normalization processor 37 as the fluorescent light image to be processed.

Thereafter, the image processing device 30 performs the variation detection process on the reflected light image of the observed region 100 (step S104). At step S104, the controller 39 controls the variation detector 35 such that it performs the variation component detection process and the filtering process on the white light image to be processed.

Under the control of the controller 39, the variation detector 35 detects the variation component of the white light image to be processed on the basis of the white light image, which is acquired from the pre-processor 33, and the old white light image, which is read from the storage unit 34, and appropriately perform the filtering process on the white light image to be processed. Specifically, the variation detector 35 divides the white light image to be processed, which is the m×n-pixel image information, to M×N-pixel blocks (M is an integer smaller than m and N is an integer smaller than n). The variation detector 35 calculates a variation vector of each pixel block of the white light image to be processed, for example, on the basis of the block matching method in which the white light image consisting of M×N-pixel blocks is set as a reference image and the old white light image that is read from the storage unit 34 is set as a reference image. The variation detector 35 calculates a variation component V(i,j) of variation vector of each pixel block as the variation component of the white light image to be processed. The variation detector 35 generates the variation component map that contains the variation component V(i,j) of each pixel block of the white light image to be processed.

The variation component V(i,j) is a variation component of a pixel block at pixel block coordinates (i,j) (i=1, 2, ..., M; j=1, 2, ..., N) of the orthogonal coordinate system of two axes of an X-axis and a Y-axis that are set to the white light image to be processed. The variation component V(i,j) is calculated from the following Equation (1).

$$V(i,j) = \sqrt{x_{ij}^2 + y_{ij}^2} \quad (1)$$

In the Equation (1), $x_{ij}$ represents an X component of the variation vector of the pixel block at the block coordinates (i,j) and $y_{ij}$ represents an Y component of the variation vector of the pixel block at the block coordinates (i,j).

The variation detector 35 performs the process for comparing the luminance value of the pixel of interest and the luminance of the neighboring pixels with respect to each pixel of the white light image to be processed, and determines whether the white light image to be processed contains a positive reflected light pixel on the basis of the result of the luminance comparison process. When the white light image to be processed contains a positive reflected light pixel, the variation detector 35 performs the filtering process for interpolating the positive reflected light pixel with the neighboring pixels. The variation detector 35 detects the variation component V(i,j) of the white light image after the filtering process and generates the variation component map that contains the variation component V(i,j) of each pixel block of the white light image after the filtering process. The variation detector 35 transmits the generated variation component map to the correction processor 36.

Subsequently, the image processing device 30 performs the correction process based on the detected variation components of the reflected light image of the observed region 100 (step S105). At step S105, the controller 39 controls the correction processor 36 such that it corrects the luminance value of the white light image to be processed taking the variation component V(i,j) that is detected by the variation detector 35 into account.

Under the control of the controller 39, the correction processor 36 corrects the luminance value taking the variation component $V_d(x,y)$ of each pixel in the variation component map into account, with respect to each corresponding pixel between the white light image to be processed, which is acquired from the pre-processor 33, and the variation component map, which is acquired from the variation detector 35. Accordingly, the correction processor 36 calculates, with respect to each pixel, a corrected luminance value $W_d(x,y)$ for which the variation component $V_d(x,y)$ in the luminance of the white light image to be processed is taken into account. The correction processor 36 transmits the corrected luminance value $W_d(x,y)$ of each pixel of the white light image to the normalization processor 37.

The variation component $V_d(x,y)$ is obtained by dividing the variation component V(i,j) of the pixel block in the variation component map to that of each pixel. The variation component $V_d(x,y)$ is a variation component at the pixel coordinates (x,y) of the two-axis orthogonal coordinate system that is set to the white light image to be processed. Because the white light image to be processed is m×n-pixel image information, the range of the pixel coordinates (x,y) of the variation component map is $1 \leq x \leq m$ and $1 \leq y \leq n$.

The image processing device 30 performs the normalization process on the fluorescent light image of the observed region 100 with the reflected light image on which the correction process is performed at step S105 (step S106). At step S106, the controller 39 controls the normalization processor 37 such that it performs the normalization process on the fluorescent light image of the observed region 100 with the white light image, on which the correction process is performed by the correction processor 36.

Under the control of the controller 39, the normalization processor 37 normalizes the luminance value of the fluorescent light image with respect to each corresponding pixel between the fluorescent light image of the observed region 100, which is acquired from the pre-processor 33, and the variation component map of the white light image, which is acquired from the correction processor 36, and accordingly generates the normalized fluorescent light image of the observed region 100. In the normalization process on the fluorescent light image, the normalization processor 37 calculates a luminance value Q(x,y) of the normalized fluorescent light image from the following Equation (2). In other words, when the corrected luminance value $W_d(x,y)$ at the pixel coordinates (x,y) is not 0, the normalization processor 37 divides, by the corrected luminance value $W_d(x,y)$, a value that is obtained by multiplying a constant K by a luminance value F(x,y) of the fluorescent light image of the observed region 100 at the pixel coordinates (x,y), thereby calculating a luminance value Q(x,y) of the normalized fluorescent light image at the pixel coordinates (x,y). In contrast, when the corrected luminance value $W_d(x,y)$ is 0, the normalization processor 37 calculates as 0 the luminance value Q(x,y) of the normalized fluorescent light image corresponding to the pixel coordinates (x,y) that is 0. The range of the pixel coordinates (x,y) is $1 \leq x \leq m$ and $1 \leq y \leq n$ as described above. The normalization processor 37 transmits the normalized fluorescent light image of the observed region 100 with the luminance value Q(x,y) to the post-processor 38.

$$\left. \begin{array}{ll} Q(x,y) = K \times F(x,y) \div W_d(x,y) & \text{if } W_d(x,y) \neq 0 \\ Q(x,y) = 0 & \text{if } W_d(x,y) = 0 \end{array} \right\} \quad (2)$$

Subsequently, the image processing device 30 performs the post-process on the normalized fluorescent light image of the observed region 100 that is generated at step S106 (step S107). At step S107, the controller 39 controls the post-processor 38 such that it performs the predetermined signal processes on the normalized fluorescent light image, which is processed by the normalization processor 37. Under the control of the controller 39, the post-processor 38 performs the signal processes, such as the gradation conversion process, the enhancement process, and the compression process, on each video signal of the normalized fluorescent light image of the observed region 100, which is acquired from the normalization processor 37, and then transmits the processed normalized fluorescent light image to the image output device 50.

Subsequently, the image processing device 30 performs the output process on the normalized fluorescent light image of the observed region 100 (step S108). At step S108, the controller 39 controls the image output device 50 such that it outputs the normalized fluorescent light image after the signal processes by the post-processor 38. Under the control of the controller 39, the image output device 50 acquires each video signal that is acquired from the post-processor 38, and displays the normalized fluorescent light image of the observed region 100 based on each of the acquired image signals.

Thereafter, when a process completion operation, such as a predetermined off operation, is performed (YES at step S109), the image processing device 30 completes the process. In this case, the input device 40 inputs instruction information for completing the process. On the basis of the input instruction information, the controller 39 completes the operation of each constituent of the image processing device 30. In contrast, when the process completion operation is not performed (NO at step S109), the image processing device 30 goes back to step S102 and repeats the process procedure from step S102 and the following steps. In this case, the controller 39 performs the process procedure from step S102 to step S109 in order to appropriately control each constituent of the image processing device 30.

Figure 7:
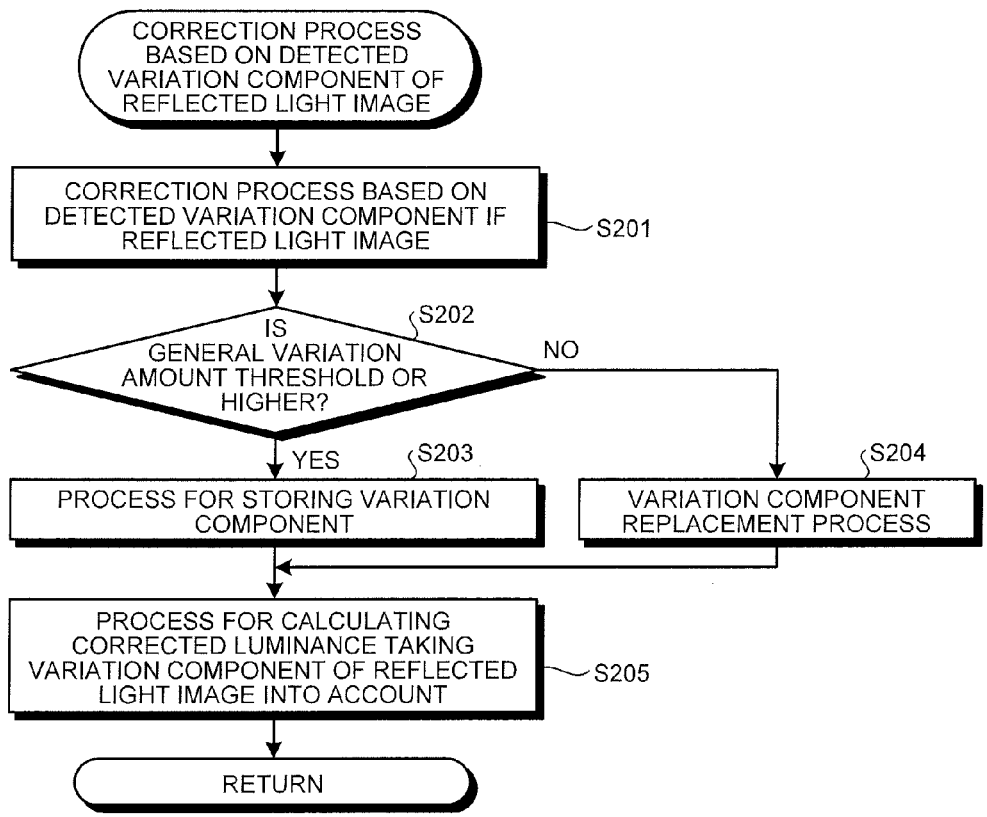
FIG. 7 is a flowchart illustrating a process procedure of a correction process that is performed by the correction processor of the image processing device according to the first embodiment of the present invention on the basis of a detected variation component of a reflected light image.

The correction process based on the detected variation component of the reflected light image at step S105 is explained in detail below. FIG. 7 is a flowchart illustrating the process procedure of the correction process based on the detected variation component of the reflected light image. As described above, under the control of the controller 39, the correction processor 36 of the image processing device 30 performs the correction process based on the detected variation component of the reflected light image at step S105.

Specifically, as represented in FIG. 7, the correction processor 36 performs the variation amount calculation process on the reflected light image to be processed (step S201). At step S201, the variation amount calculator 36a acquires the variation component map of the white light image of the observed region 100, which is the reflected light image to be processed, from the variation detector 35. As described above, the acquired variation component map contains the variation component $V(i,j)$ of each pixel block, which is obtained by dividing the white light image to be processed to m×n-pixel blocks. The variation amount calculator 36a calculates a general variation amount $V_{ave}$ of the white light image to be processed on the basis of the variation component $V(i,j)$ of each pixel in the acquired variation component map. The variation amount calculator 36a transmits the calculated general variation amount $V_{ave}$ of the white light image to be processed to the replacement processor 36b. The general variation amount $V_{ave}$ of the white light image to be processed is calculated, for example, from the following Equation (3).

$$V_{ave} = \frac{\sum_{i=0}^{M} \sum_{j=0}^{N} V(i,j)}{M \times N} \quad (3)$$

Subsequently, the correction processor 36 determines whether the general variation amount $V_{ave}$ of the white-light image to be processed, which is calculated at step S201, is a predetermined threshold $V_t$ or higher (step S202). At step S202, the replacement processor 36b acquires the general variation amount $V_{ave}$ of the white light image to be processed from the variation amount calculator 36a. The replacement processor 36b acquires the variation component map of the white light image to be processed from the variation detector 35. The replacement processor 36b performs the compares the acquired general variation amount $V_{ave}$ and the threshold $V_t$. When the general variation amount $V_{ave}$ is the threshold $V_t$ or higher, the replacement processor 36b determines that the object in the white light image to be processed, which corresponds to the variation component map, has the predetermined variation or more. In contrast, when the general variation amount $V_{ave}$ is lower than the threshold $V_t$, the replacement processor 36b determines that the object in the white light image to be processed, which corresponds to the variation component map, does not have the predetermined variation or more.

When the general variation amount $V_{ave}$ is the threshold $V_t$ or higher at step S202 (YES at S202), the correction processor 36 performs a process for storing the variation component of the white light image to be processed (step S203). At step S203, the replacement processor 36b outputs the variation component map of the white light image to be processed to the corrected luminance calculator 36d, and outputs the variation component map to the variation component storage unit 36c as the variation component map that is obtained when the object has the predetermine variation or more. The variation component storage unit 36c stores the variation component map that is acquired from the replacement processor 36b and updates the variation component map every time the variation component storage unit 36c acquires a variation component map from the replacement processor 36b.

In contrast, when the general variation amount $V_{ave}$ is lower than the threshold $V_t$ at step S202 (NO at S202), the correction processor 36 performs a variation component replacement process on the white light image to be processed (step S204). At step S204, the replacement processor 36b reads the old variation component map from the variation component storage unit 36c and replaces the variation component map of the white light image to be processed, which is acquired from the variation detector 35, with the old variation component map. In other words, the replacement processor 36b replaces the variation component map that does not have the predetermined variation or more with the variation component map that is obtained when the subject has the predetermined variation or more. In this case, the replacement processor 36b outputs the old variation component map to the corrected luminance calculator 36d as the variation component map of the white light image to be processed.

Thereafter, the correction processor 36 performs a corrected luminance calculating process taking the variation component of the reflected light image to be processed (step S205) into account. At step S205, the corrected luminance calculator 36d acquires the white light image to be processed from the pre-processor 33, and acquires the correction component map from the replacement processor 36b. The corrected luminance calculator 36d divides the M×N-pixel block that is contained in the acquired variation component map to the original pixel units, i.e., to m×n pixels, and calculates the variation component $V_d(x,y)$ of each of the divided pixels. In this case, the corrected luminance calculator 36d sets equal values to the variation component $V(i,j)$ before division of the variation component map and to the variation component $V_d(x,y)$ of each of the pixels that is obtained by dividing the pixel block. Subsequently, the corrected luminance calculator 36d calculates the corrected luminance value $W_d(x,y)$, taking the variation component $V_d(x,y)$ of the pixel unit of the variation component map into account, with respect to each corresponding pixel between the white light image to be processed and the variation component map. Specifically, as represented by the following Equation (4), the corrected luminance calculator 36d adds the value that is obtained by multiplying a constant by the luminance value $W(x,y)$ of the white light image to be processed to the value that is obtained by multiplying a constant b by the variation component $V_d(x,y)$ with respect to each set of pixel coordinates (x,y) in order to calculate the corrected luminance value $W_d(x,y)$ of each pixel of the white light image. The corrected luminance calculator 36d transmits the corrected luminance value $W_d(x,y)$ of each pixel of the white light image, which is calculated as described above, to the normalization processor 37.

$$W_d(x,y) = a \times W(x,y) + b \times V_d(x,y) \quad (4)$$

The luminance value $W(x,y)$ of Equation (4) is a luminance value of the pixel at the pixel coordinates (x,y) (x=1, 2, ..., m; y=1, 2, ..., n) in the two-axis orthogonal coordinate system that is set to the white light image to be processed. The constants a and b may be set by the controller 39 on the basis of information that is input by the input device 40 or may be automatically set by the controller 39, for example, on the basis of the gain of the focal distance of the objective lens 23.

After completing the process procedure at step S205, the correction processor 36 returns to step S105 represented in FIG. 6. Thereafter, the image processing device 30 goes to step S106 and performs the process procedure from step S106 and the following steps as described above.

Figure 8:
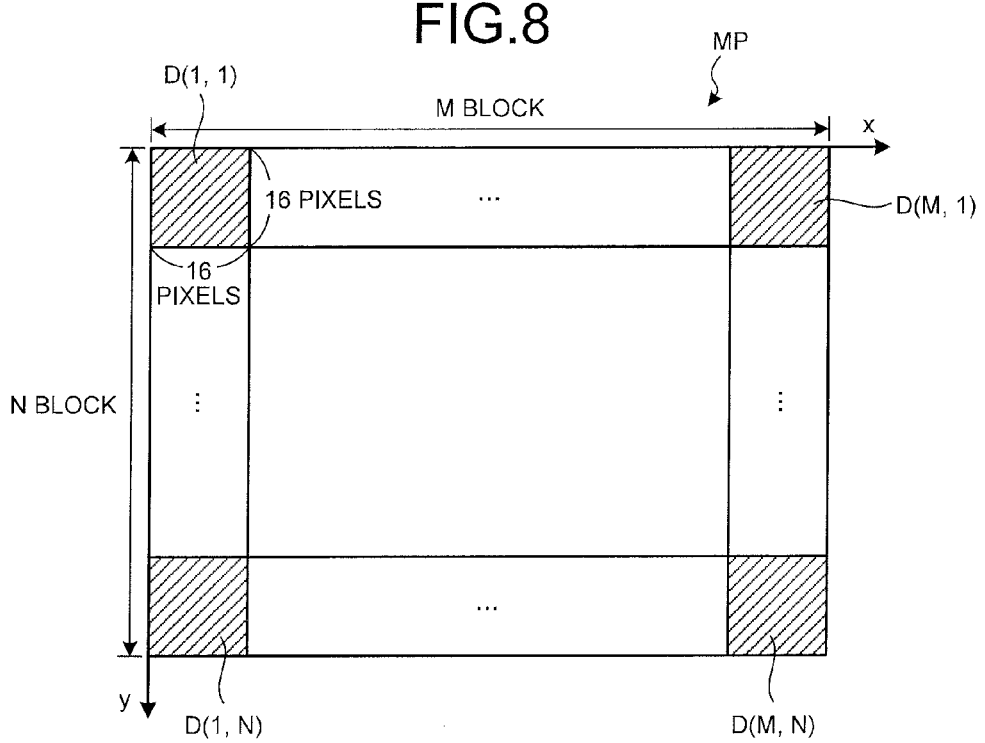
FIG. 8 is a schematic diagram representing a specific example of a variation component map of a white light image to be processed, which is generated by a variation detector of the image processing device according to the first embodiment of the present invention.
Figure 9:
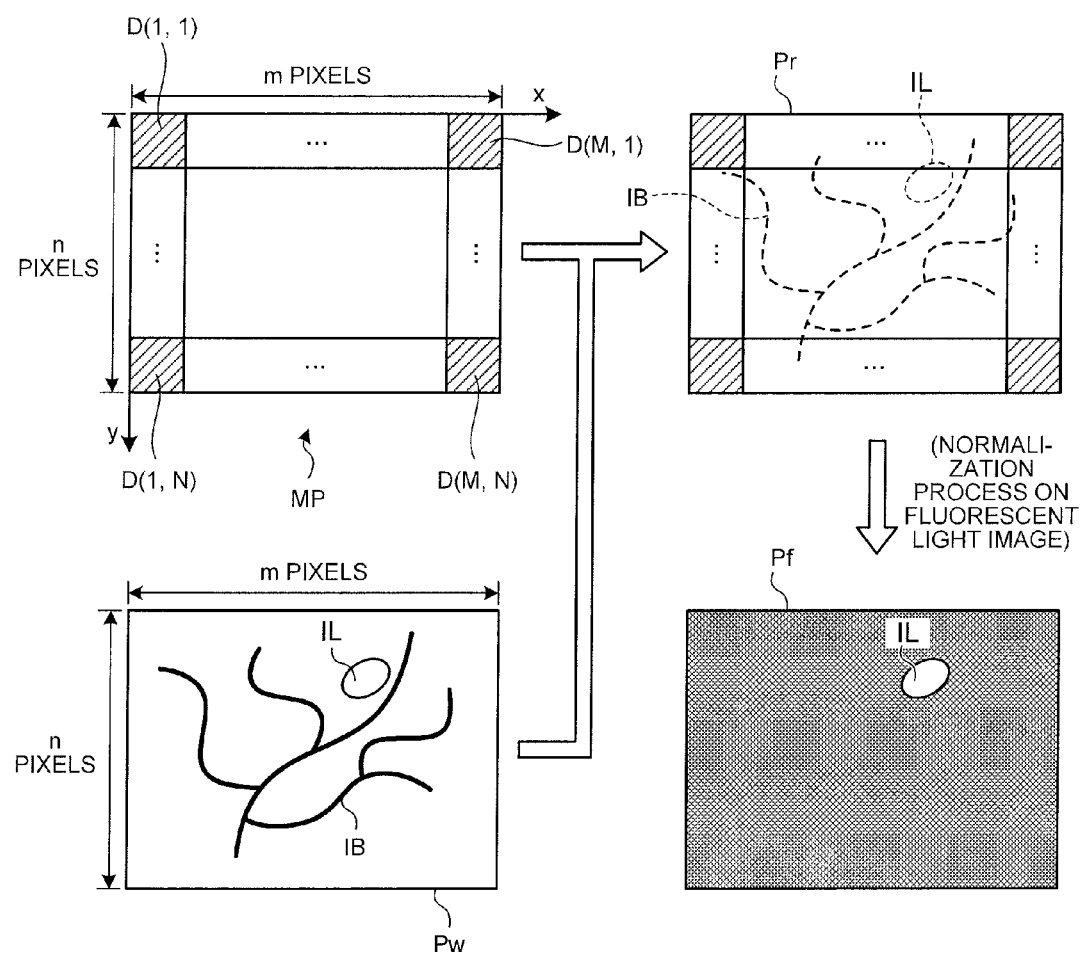
FIG. 9 is a schematic diagram representing how the correction processor of the image processing device according to the first embodiment of the present invention performs the correction process on the white light image taking the variation component into account.

The correction process that is performed by the correction processor 36 on the white light image to be processed is specifically explained taking as an example a case where each pixel block that is contained in the m×n-pixel variation component map is a 16×16-pixel block. FIG. 8 is a schematic diagram representing a specific example of the variation component map of the white light image to be processed. FIG. 9 is a schematic diagram representing a state where the correction process is performed on the white light image taking the variation component into account.

As represented in FIG. 8, a variation component map MP of the white light image to be processed, which is generated by the variation detector 35, is formed of pixel blocks D(i,j) of M×N blocks of which pixel block unit is 16×16 pixels. The pixel blocks D(i,j) is a pixel block at block coordinates (i,j) (1≤i≤M, 1≤j≤N) of the two-axis orthogonal coordinate system of the x-axis and y-axis that is set in the variation component map MP. For example, the pixel block D(1,1) is the pixel block at the block coordinates (1,1) of the variation component map MP, and the pixel block D(M,N) is the pixel block at the block coordinates (M,N) of the variation component map MP.

The two-axis orthogonal coordinate system that is set in the variation component map MP has the x-axis as the horizontal axis of the variation component map MP and the y-axis as the vertical axis of the variation component map MP as represented in FIG. 8. In the two-axis orthogonal coordinate system, the rightward direction of the x-axis from the origin of the upper left corner of the variation component map MP represented in FIG. 8 is the positive direction, and the downward direction of the y-axis from the origin of the upper left corner of the variation component map MP is the positive direction. In the variation component map MP, the number of blocks in the horizontal axis is represented by M=m pixels/16, and the number of blocks in the vertical axis is represented by M=n pixels/16.

The variation component map MP of M×N blocks further contains the variation component V(i,j), which is calculated by the variation detector 35, in every pixel block D(i,j). For example, in the variation component map MP, the variation component of the pixel block D(1,1) is V(1,1), the variation component of the pixel block D(M,1) is V(M,1), the variation component of the pixel block D(1,N) is V(1,N), and the variation component of the pixel block D(M,N) is V(M,N). The variation component V(i,j) of the pixel block D(i,j) is calculated from Equation (1).

The correction processor 36 corrects the luminance value of the white light image to be processed taking the variation component V(i,j) in the variation component map MP into account. In the correction processor 36, the corrected luminance calculator 36d acquires a m×n-pixel white light image Pw to be processed and the variation component map MP. First, the corrected luminance calculator 36d divides each pixel block D(i,j) in the variation component map MP to m×n pixels that are the original pixel units. Specifically, the corrected luminance calculator 36d divides each of the pixel blocks D(1,1) to D(M,N) to 16×16 pixels.

Subsequently, the corrected luminance calculator 36d calculates the variation component $V_d(x,y)$ of each of the divided pixels. In this case, the corrected luminance calculator 36d sets equal values to the variation component V(i,j) of the pixel block D before being divided and the variation component $V_d(x,y)$ of each of the pixels that are divided from the pixel block D(i,j). For example, the value of the variation component $V_d(x,y)$ of each of the 16×16 pixels that are divided from the pixel block D(1,1) is equal to the value of the variation component V(1,1), and the value of the variation component $V_d(x,y)$ of each of the 16×16 pixels that are divided from the pixel block D(M,N) is equal to the value of the variation component V(M,N).

In this manner, after calculating the variation component $V_d(x,y)$ of each pixel of the variation component map MP, the corrected luminance calculator 36d calculates the corrected luminance value $W_d(x,y)$ taking the variation component $V_d(x,y)$ into account with respect to each corresponding pixel between the white light image Pw to be processed and the variation component map MP. The corrected luminance calculator 36d then generates a normalization image Pr that contains the calculated corrected luminance value $W_d(x,y)$ of each pixel (see FIG. 9). In this manner, the correction processor 36 achieves the correction process on the white light image Pw taking the variation component $V_d(x,y)$ of each pixel of the variation component map MP into account.

The corrected luminance value $W_d(x,y)$ of each pixel of the normalization image Pr, which is the white light image after the correction process is transmitted to the normalization processor 37 and is used for the normalization process on a fluorescent light image Pf of the observed region 100. The variation component $V_d(x,y)$ that is contained in the corrected luminance value $W_d(x,y)$ is a value that varies depending on the imaging distance between the observed region 100, which is the object, and the reflected light imaging unit 26. Specifically, the variation component $V_d(x,y)$ decreases with an increase in imaging distance and increases with a decrease in imaging distance. The normalization image Pr that contains, with respect to every pixel, the corrected luminance value $W_d(x,y)$ for which the variation component $V_d(x,y)$ is taken into account has a luminance distribution that accurately reflects the imaging distance between the observed region 100, which is the object, and the reflected light imaging unit 26 regardless of whether there is a positive reflected light pixel.

By performing the normalization process on the luminance value of the fluorescent light image Pf of the observed region 100 with respect to each corresponding pixel, with the corrected luminance value $W_d(x,y)$ of the normalization image Pr, the normalization processor 37 can accurately corrects the brightness and darkness (the luminance value) in the fluorescent light image Pf, which varies depending on the imaging distance between the observed region 100 and the fluorescent light imaging unit 28, without influence of positive reflected light from the observed region 100. In the fluorescent light image Pf on which the normalization process is performed (i.e., the normalized fluorescent light image), an image IL of the lesion 101, from which the fluorescent light is generated due to application of the excitation light, is drawn in pixels with relatively high luminance regardless of the imaging distance between the observed region 100 and the fluorescent light imaging unit 28.

The white light image Pw and fluorescent light image Pf to be processed are information of the images of the observed region 100 that are captured at the same timing. Thus, the position of the object, such as the lesion 101, coincides between the white light image Pw and the fluorescent light image Pf. Using the normalization image Pr that corresponds to the white light image Pw, the normalization processor 37 can normalize the luminance value of the fluorescent light image Pf with high accuracy. The reference character "IB" represented in FIG. 9 denotes an image of blood vessels.

As explained above, in the first embodiment of the present invention, the white light image of the observed region, which is based on the white light reflected from the observed region, and the fluorescent light image of the observed region, which is based on the fluorescent light generated from the observed region, are firstly acquired as the image information to be processed. The variation component of the white light image to the processed is detected on the basis of the old white light image of the observed region, which was acquired before, and the white light image to be processed. Taking the detected variation component into account, the luminance value of the white light image to be processed is corrected. With the corrected luminance value, the luminance of the fluorescent light image is normalized. Accordingly, the variation component of pixel that varies depending on the in imaging distance to the object can be taken into account for the luminance value of the white light image to be processed. This leads to generation of the normalization image with the luminance distribution that accurately reflects the imaging distance to the object regardless of whether there is a positive reflected light pixel. By performing the normalization process on the luminance value of the fluorescent light image to be processed, using the luminance value of the normalization image, luminance of the fluorescent light image to be observed can be accurately corrected. Accordingly, an abnormal tissue, such as the lesion, in the observed region can be clearly drawn in the fluorescent light image, which increases the capability of detecting an abnormal tissue in the subject using the fluorescent light image and increases the diagnostic capability.

In the first embodiment, the luminance value of the fluorescent light image is normalized using the normalization image that corresponds to the white light image of the observed region, which is captured at the same timing as that of the fluorescent light image of the observed region. Thus, without effect of positional shift of the object between the images, the luminance value of the fluorescent light image can be corrected with high accuracy.

Second Embodiment

A second embodiment of the present invention is explained below. In the first embodiment, the fluorescent light image and the white light image of the observed region 100, which are captured at the same timing, are acquired, and the normalization process is performed on the fluorescent light image using the corrected luminance value that is calculated taking the variation component of the white light image into account. In the second embodiment, a white light image and a fluorescent light image of the observed region 100 that are captured at different timing are acquired. In addition, the variation component of the white light image is compensated for to the variation component at the timing at which the fluorescent light image is acquired, and the normalization process is performed on the fluorescent light image of the observed region 100, using the corrected luminance value of the white light image that is calculated taking the compensated variation component into account.

Figure 10:
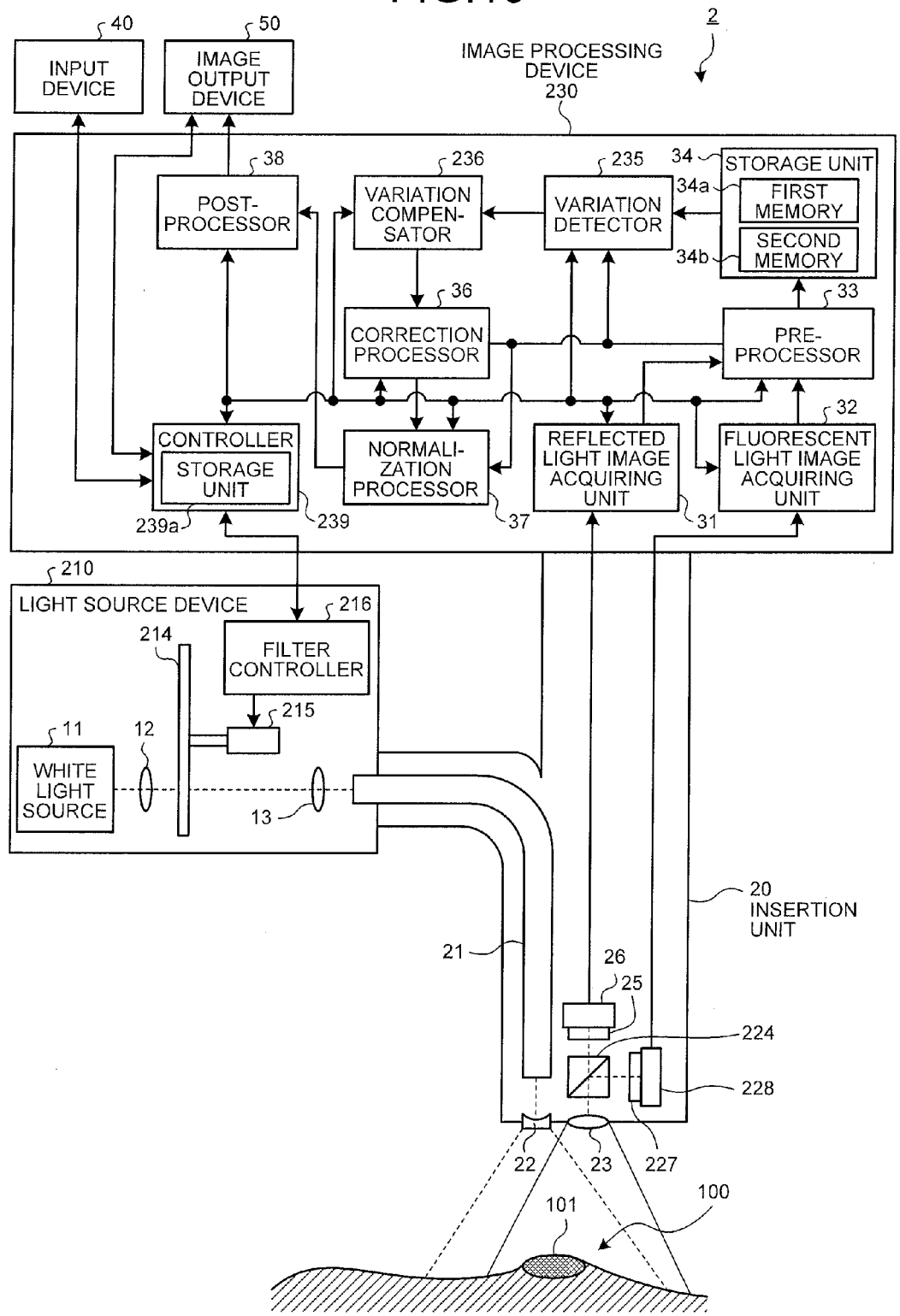
FIG. 10 is a block diagram schematically representing an example of a configuration of an endoscope according to a second embodiment of the present invention.

FIG. 10 is a block diagram schematically representing an example of a configuration of an endoscope according to the second embodiment of the present invention. As represented in FIG. 10, an endoscope 2 according to the second embodiment includes a light source device 210 instead of the light source device 10 of the endoscope 1 according to the first embodiment; a half mirror 224 instead of the dichroic mirror 24; and a barrier filter 227 instead of the barrier filter 27. The endoscope 2 further includes a fluorescent light imaging unit 228 instead of the fluorescent light imaging unit 28; and an image processing device 230 instead of the image processing device 30. In the endoscope 2, the light source device 210 includes a rotation filter 214 that switches the illuminating light to the observed region 100 from excitation light to white light or vise versa; a motor 215 that is a driver of the rotation filter 214; and a filter controller 216 that controls filter switching in the optical path by rotating the rotation filter 214. The image processing device 230 further includes a variation detector 235 instead of the variation detector 35 of the image processing device 30 according to the first embodiment; and a controller 239 instead of the controller 39, and further includes a variation compensator 236. Other aspects of the configuration are the same as those of the first embodiment, and accordingly, the same constituents are denoted by the same reference numbers.

The light source device 210 functions as a light source unit that applies excitation light that excites a fluorescent agent and white light, which is an example of illuminating light, alternately to the observed region 100. Specifically, the light source device 210 includes the rotation filter 214, the motor 215, and the filter controller 216, in addition to the white light source 11, the collimating lens 12, and the condenser lens 13.

Figure 11:
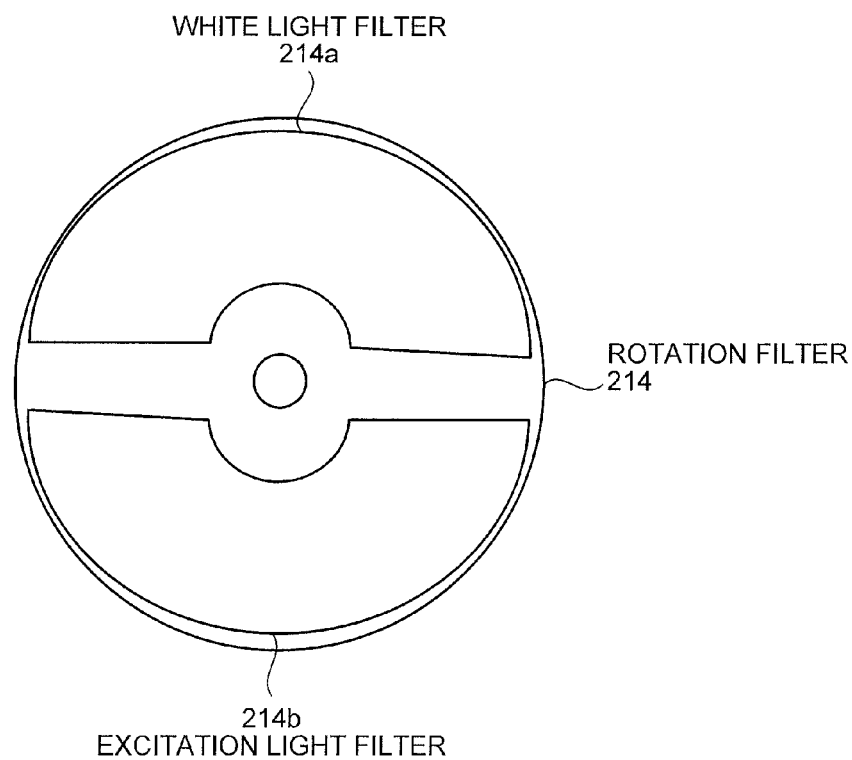
FIG. 11 is a schematic diagram representing an example of a configuration of a rotation filter according to the second embodiment of the present invention.
Figure 12:
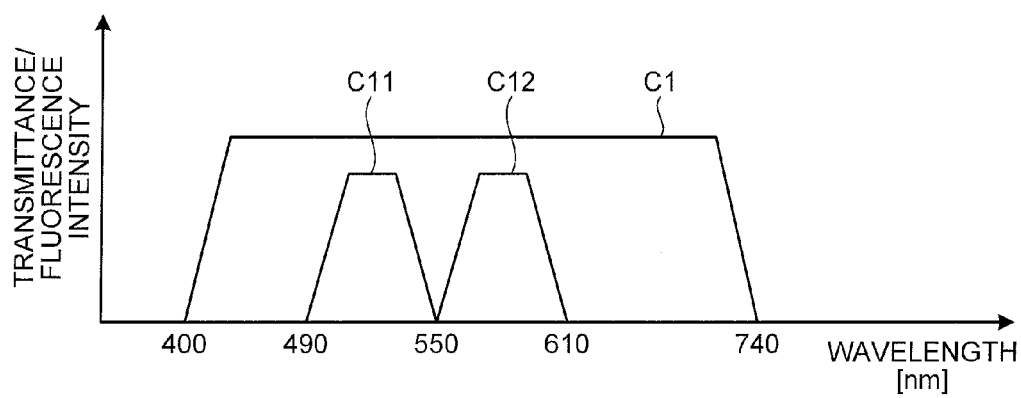
FIG. 12 is a schematic diagram representing an example of transmittance properties of the rotation filter according to the second embodiment of the present invention.

The rotation filter 214 extracts light in a predetermined wavelength band from the white light that is emitted by the white light source 11. FIG. 11 is a schematic diagram representing an example of a configuration of the rotation filter. FIG. 12 is a schematic diagram representing an example of transmittance properties of the rotation filter. FIG. 12 illustrates a correlation line C12 of wavelength with respect to intensity that illustrates spectral properties of the fluorescent light that is generated due to the excitation light, which is extracted by the rotation filter 214. As illustrated in FIG. 11, the rotation filter 214 includes a white light filter 214a and an excitation light filter 214b with different spectral properties.

The white light filter 214a allows the white light in the predetermined wavelength band out of the white light that is emitted by the white light source 11 to pass thorough. Specifically, the white light filter 214a has transmittance properties that allow the white light in a wavelength band of 400 to 740 nm to pass through as represented by the correlation line C1 of wavelength with respect to transmittance, which is represented in FIG. 12. The white light filter 214a with such transmittance properties extracts white light in the wavelength band of 400 to 740 nm from the light emitted by the white light source 11 and allows the extracted white light to pass through as the illuminating light to the observed region 100.

The excitation light filter 214b allows the excitation light in the predetermined wavelength band out of the white light that is emitted by the white light source 11 to pass thorough. Specifically, the excitation light filter 214b has transmittance properties that allow the excitation light in a wavelength band of 490 to 550 nm to pass through as represented by the correlation line C11 of wavelength with respect to transmittance represented in FIG. 12. The excitation light filter 214b with such transmittance properties extracts the excitation light in the wavelength band of 490 to 550 nm from the white light that is emitted by the white light source 11 and allows the extracted excitation light to pass through. The excitation light that is extracted by the excitation light filter 214b excites the fluorescent agent that is specifically accumulated on the lesion 101, such as a tumor, existing in the observed region 100 to cause generation of fluorescent light in the wavelength band, for example, of 550 to 610 nm (see the correlation line C12 represented in FIG. 12).

The rotation filter 214 that includes the white light filter 214a and the excitation light filter 214b is driven by the motor 215 to rotate in the circumferential direction. This switches between the white light filter 214a and the excitation light filter 214b and positions them alternately in the optical path of the white light from the white light source 11 (see the dotted line in the light source device 210 represented in FIG. 10). In the state where the white light filter 214a is positioned in the optical path, the rotation filter 214 allows the white light of 400 to 740 nm to pass through. In the state where the excitation light filter 214b is positioned in the optical path, the rotation filter 214 allows the excitation light of 490 to 550 nm to pass through. In other words, the rotation filter 214 allows white light and excitation light to pass through alternately.

The excitation light filter 214b of the rotation filter 214 is not limited to one that has the transmittance properties illustrated by the correlation line C11 represented in FIG. 12. The excitation light filter 214b may have arbitrary transmittance properties as long as it allows fluorescent light that causes generation of excitation light that causes generation of fluorescent light from the observed region 100 to pass through. In this case, the transmittance wavelength band of the excitation light filter 214b may be a desired wavelength band in the wavelength band of visible light or may be a desired wavelength band out of the visible-light wavelength band.

The filter controller 216 controls filter switching in the optical path by rotating the rotation filter 214. Specifically, the filter controller 216 controls driving of the motor 215 to rotate that is connected to the rotation filter 214 via the rotation shaft, and controls driving of the rotation filter 214 to rotate through the drive control on the motor 215. The filter controller 216 causes the white light filter 214a and the excitation light filter 214b to be positioned alternately in the optical path of the white light from the white light source 11 at a predetermined time interval. In this manner, the filter controller 216 controls filter switching of the rotation filter 214 in the optical path. In addition, the filter controller 216 knows which of the white light filter 214a and the excitation light filter 214b is positioned in the optical path on the basis of the rotation drive state, such as the rotational speed of the motor 215. The filter controller 216 transmits filter information that represents the filter positioned in the optical path (the white light filter 214a or the excitation light filter 214b) to the controller 239 of the image processing device 230. The operations of the filter controller 216 are controlled by the controller 239 of the image processing device 230 to be described below.

The white light and excitation light that are alternately emitted by the light source device 210 with the above configuration are alternately applied to the observed region 100 via the light guide fiber 21 of the insertion unit 20 at the predetermined time interval.

The half mirror 224 reflects the light from the observed region 100, which passes the objective lens 23, to the side of the reflected light imaging unit 26 and the side of the fluorescent light imaging unit 228 equally. Specifically, when the white light from the light source device 210 is applied to the observed region 100, the half mirror 224 reflects the white light, which is reflected from the observed region 100, to the optical path of the reflected light imaging unit 26 and the optical path of the fluorescent light imaging unit 228. In contrast, when the excitation light from the light source device 210 is applied to the observed region 100, the half mirror 224 reflects the fluorescent light, which is generated from the observed region 100, and the excitation light, which is reflected from the observed region 100, to the optical path of the reflected light imaging unit 26 and the optical path of the fluorescent light imaging unit 228.

Figure 13:
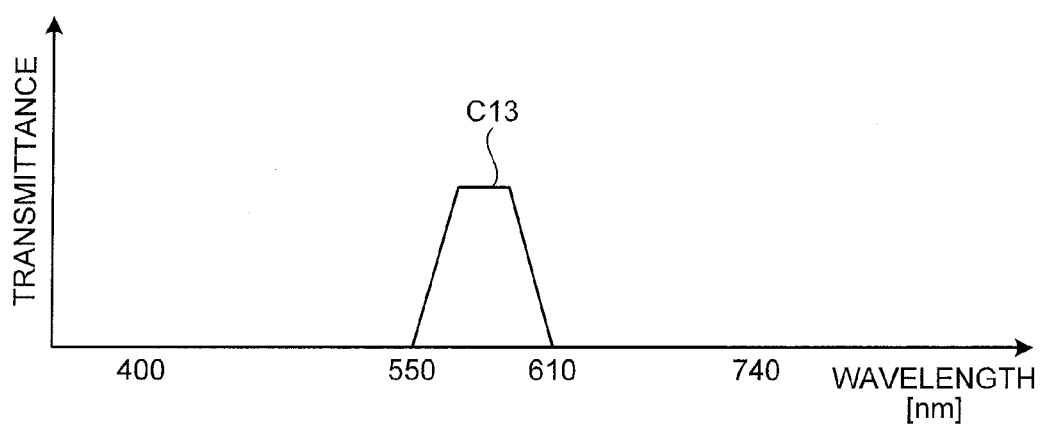
FIG. 13 is a schematic diagram representing an example of transmittance properties of a barrier filter according to the second embodiment of the present invention.

The barrier filter 227 allows only the fluorescent light from the observed region 100 that is reflected by the half mirror 224 to the optical path of the fluorescent light imaging unit 228 to pass through, and cuts off light (for example, the excitation light) other than this fluorescent light. FIG. 13 is a schematic diagram representing an example of transmittance properties of the barrier filter according to the second embodiment. The barrier filter 227 has transmittance properties that allow light in the wavelength band of 550 to 610 nm as represented by the correlation line C13 of wavelength with respect to transmittance represented in FIG. 13. The barrier filter 227 with such transmittance properties cuts off the white light and the excitation light, that are reflected from the observed region 100, out of the light from the observed region 100 that is reflected by the half mirror 224 to the optical path of the fluorescent light imaging unit 228, and the barrier filter 227 allows the fluorescent light from the observed region 100, i.e., light in the wavelength band of 550 to 610 nm, to pass through.

The fluorescent light imaging unit 228 captures a fluorescent light image of the observed region 100 at timing different from that of the reflected light imaging unit 26. Specifically, when the excitation light from the light source device 210 is applied to the observed region 100, the fluorescent light imaging unit 228 receives the fluorescent light from the observed region 100 that is reflected by the half mirror 224 to the optical path of the fluorescent light imaging unit 228, i.e., receives the fluorescent light that passes through the barrier filter 227. Accordingly, the fluorescent light imaging unit 228 captures the fluorescent light image of the observed region 100 at the timing at which the excitation light is applied to the observed region 100. When the white light out of the light that is emitted alternately from the light source device 210 at the predetermined interval is applied to the observed region 100, the reflected light imaging unit 26 receives the white light from the observed region 100 that is reflected by the half mirror 224 to the optical path of the reflected light imaging unit 26 in order to capture the white light image of the observed region 100. In other words, the fluorescent light imaging unit 228 captures the fluorescent light image of the observed region 100 at the timing at the predetermined interval from the timing at which the white light image is captured. The fluorescent light imaging unit 228 has functions similar to those of the fluorescent light imaging unit 28 according to the first embodiment, in addition to the function of capturing a fluorescent light image at the timing different from that of the reflected light imaging unit 26.

As described above, the image processing device 230 includes the variation detector 235 instead of the variation detector 35 according to the first embodiment and the controller 239 instead of the controller 39 according to the first embodiment, and further includes the variation compensator 236. The image processing device 230 has functions similar to those of the image processing device 30 according to the first embodiment, in addition to the functions of the variation detector 235, the variation compensator 236, and the controller 239.

On the basis of two frames of reflected light image of the observed region 100 that are sequentially acquired by the reflected light image acquiring unit 31 chronologically, the variation detector 235 detects a variation component of the reflected light image to be processed. Specifically, the variation detector 235 acquires the white light image of the observed region 100 that is processed by the pre-processor 33 (the white light image to be processed) from the pre-processor 33. The variation detector 235 reads the white light image of the observed region 100 that is captured a desired number of frames (for example, one frame) prior to the white light image to be processed (the old white light image) from the storage unit 34. The white light image to be processed and the old white light image are white light images of the observed region 100 that are sequentially captured at each timing at which white light is applied from the light source device 210 to the observed region 100 at the predetermined time interval, and the images are chronologically continuous. The variation detector 235 detects the variation component the white light image to be processed, for example, with the block-matching method on the basis of the white light image to be processed and the old white light image that are continuous chronologically. The variation detector 235 detects, with respect to each pixel or each pixel block, a variation vector between the white light image to be processed and the old white light image, which are continuous chronologically, and calculates a representative vector of the detected variation vectors. The representative vector that is calculated by the variation detector 235 may be the average of the variation vectors of pixels or pixel blocks or may be the median. The variation detector 235 transmits the variation component map of the white light image to be processed and the representative vector to the variation compensator 236. The variation detector 235 has functions similar to those of the variation detector 35 according to the first embodiment in addition to the function of detecting a variation component and a representative vector.

The variation compensator 236 compensates for the variation component of the reflected light image to be processed that is detected by the variation detector 235 to the variation component at the same timing as that when the fluorescent light image is captured. Specifically, the variation compensator 236 acquires the variation component map and the representative vector of the white light image to be processed, which are detected by the variation detector 235. The variation compensator 236 calculates the variation compensation vector on the basis of the representative vector, which is acquired from the variation detector 235, and the intervals at which the white light image and the fluorescent light image of the observed region 100 are captured. The variation compensation vector is vector information that represents the difference between each variation vector of the white light image to be processed and each variation vector of the white light image to be processed at the timing at which the fluorescent light image to be processed is captured. On the basis of the variation component map and variation compensation vector of the white light image to be processed, the variation compensator 236 compensates for each variation component in the variation component map to the variation component at the timing at which the fluorescent light image of the observed region 100 is captured. The variation compensator 236 transmits the variation component map after the variation compensation process to the correction processor 36.

As in the case of the controller 39 of the image processing device 30 according to the first embodiment, the controller 239 is achieved with a storage unit 239a that stores predetermined process programs including an image processing program, and a computer that executes the process programs in the storage unit 239a. The storage unit 239a is a computer-readable storage medium according to the second embodiment. On the basis of instruction information that is input by the input device 40, the controller 239 controls the filter controller 216 such that it performs filter switch control on the rotation filter 214 of the light source device 210.

The controller 239 sequentially acquires the filter information from the filter controller 216. Based on the acquired filter information, the controller 239 determines which of the white light filter 214a and the excitation light filter 214b is the rotation filter 214 that is currently positioned in the optical path of the light source device 210. When the filter in the optical path of the light source device 210 is the white light filter 214a, the controller 239 controls the reflected light image acquiring unit 31 such that it acquires the white light image of the observed region 100 that is captured by the reflected light imaging unit 26 at the timing at which the white light is applied to the observed region 100. When the filter in the optical path of the light source device 210 is not the white light filter 214a, the controller 239 controls the reflected light image acquiring unit 31 such that it eliminates video signals from the reflected light imaging unit 26. In contrast, when the filter in the optical path of the light source device 210 is the excitation light filter 214b, the controller 239 controls the fluorescent light image acquiring unit 32 such that it acquires the fluorescent light image of the observed region 100 that is captured by the fluorescent light imaging unit 228 at the timing at which the excitation light is applied to the observed region 100. When the filter in the optical path of the light source device 210 is not the excitation light filter 214b, the controller 239 controls the fluorescent light image acquiring unit 32 such that it eliminates video signals from the fluorescent light imaging unit 228. In this manner, the controller 239 controls the reflected light image acquiring unit 31 and the fluorescent light image acquiring unit 32 such that they acquire white light images and fluorescent light images of the observed region 100 alternately at the predetermined time interval.

The controller 239 also controls a variation detecting process and a representative vector calculation process that are performed by the variation detector 235 on the white light image to be processed, and the variation compensation process that is performed by the variation compensator 236 on the white light image to be processed. The controller 239 controls the correction processor 36 such that it performs the luminance correction process on the white light image to be processed on the basis of the variation component map after the variation compensation process that is performed by the variation compensator 236. The controller 239 has functions similar to those of the controller 39 of the image processing device 30 according to the first embodiment in addition to each of the control functions according to the second embodiment.

Figure 14:
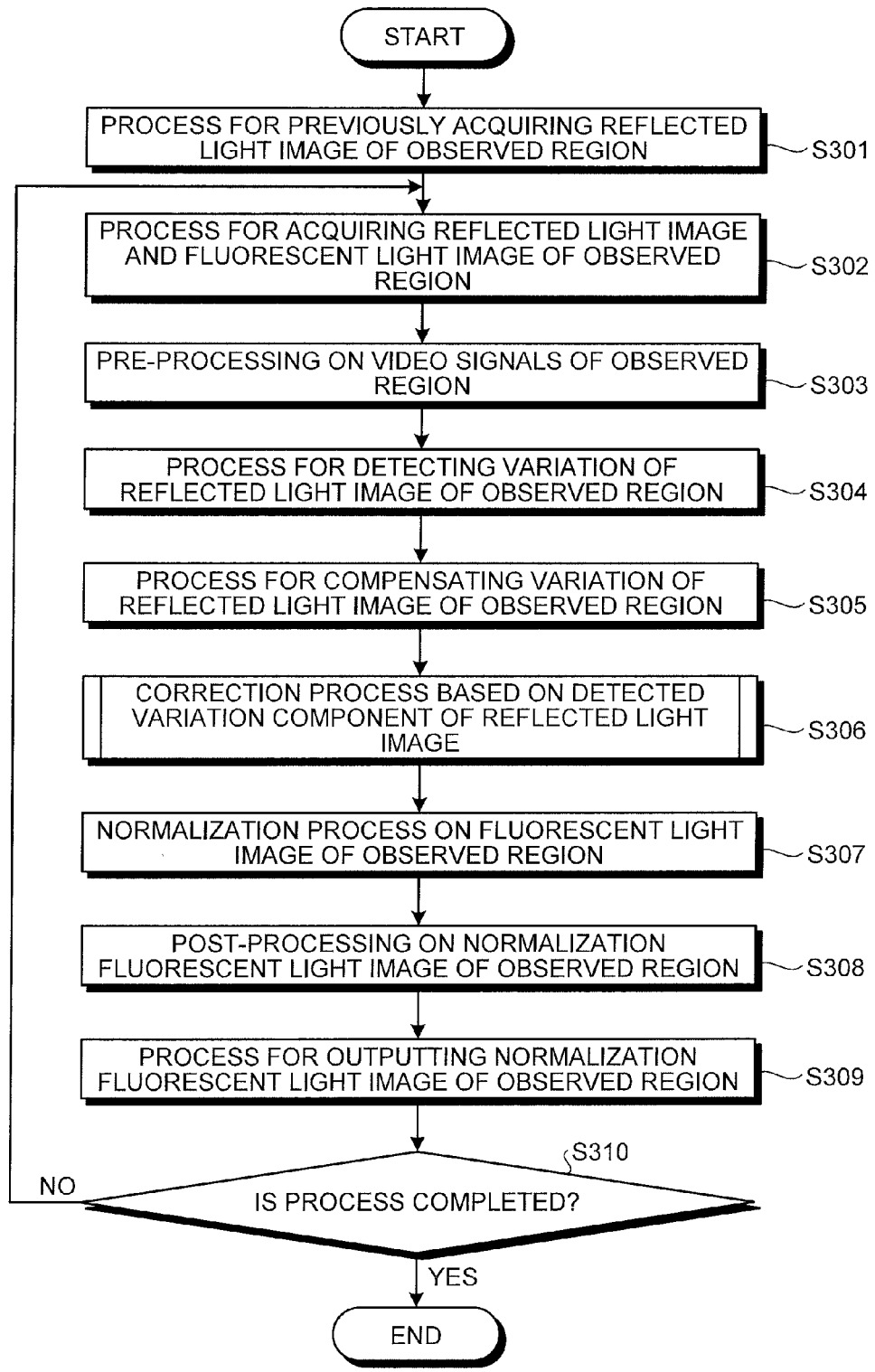
FIG. 14 is a flowchart illustrating a process procedure of an image processing device according to the second embodiment of the present invention.

Operations of the image processing device 230 according to the second embodiment of the present invention are explained below. FIG. 14 is a flowchart illustrating the process procedure of the image processing device according to the second embodiment of the present invention. FIG. 15 is a schematic diagram for specifically explaining the operations of the image processing device according to the second embodiment.

As illustrated in FIG. 14, first, the image processing device 230 previously acquires a reflected light image of the observed region 100 (step S301). At step S301, the controller 239 controls the filter controller 216 such that white light is applied from the light source device 210 to the observed region 100 and controls the reflected light image acquiring unit 31 such that it acquires the white light image of the observed region 100 at the timing at which the white light is applied.

Under the control of the controller 239, the filter controller 216 controls the motor 215 such that the white light filter 214a of the rotation filter 214 is positioned in the optical path of the light source device 210. Accordingly, the white light emitted by the light source device 210 is applied to the observed region 100. On the other hand, under the control of the controller 239, the reflected light image acquiring unit 31 acquires a white light image Pw1 of the observed region 100 that is captured by the reflected light imaging unit 26 at timing T1 when the white light from the light source device 210 is applied to the observed region 100, and the reflected light image acquiring unit 31 transmits each video signal of the acquired white light image Pw1 after digital conversion to the pre-processor 33. Under the control of the controller 239, the pre-processor 33 performs the above-described signal processes on each video signal of the white light image Pw1 that is acquired from the reflected light image acquiring unit 31, and then transmits each video signal of the white light image Pw1 to the storage unit 34. The storage unit 34 stores the white light image Pw1 of the observed region 100 that is acquired from the pre-processor 33 as the white light image older than a white light image Pw2 of the observed region 100 (see FIG. 15) to be processed subsequently.

The timing T1 is before timing T2 at which the excitation light from the light source device 210 is applied to the observed region 100. The white light image Pw1 of the observed region 100 that is captured at the timing T1 is image information older than that of the fluorescent light image Pf of the observed region 100 that is captured at the timing T2.

The image processing device 230 acquires the reflected light image and the fluorescent light image of the observed region 100 that are to be processed (step S302). At step S302, the controller 239 first controls the filter controller 216 such that the excitation light is applied from the light source device 210 to the observed region 100, and controls the fluorescent light image acquiring unit 32 such that it acquires the fluorescent light image of the observed region 100 at the timing at which the excitation light is applied. Subsequently, the controller 239 controls the filter controller 216 such that the white light is applied from the light source device 210 to the observed region 100, and controls the reflected light image acquiring unit 31 such that it acquires the white light image of the observed region 100 at the timing at which the white light is applied.

Under the control of the controller 239, the filter controller 216 controls the motor 215 such that the excitation light filter 214b of the rotation filter 214 is positioned in the optical path of the light source device 210. Accordingly, the excitation light from the light source device 210 is applied to the observed region 100. Under the control of the controller 239, the fluorescent light image acquiring unit 32 then acquires the fluorescent light image Pf of the observed region 100 that is captured by the fluorescent light imaging unit 228 at the timing T2 at which the excitation light from the light source device 210 is applied to the observed region 100, and transmits each video signal of the acquired fluorescent light image Pf after digital conversion to the pre-processor 33. After application of the excitation light on the observed region 100, the filter controller 216 controls the motor 215 such that the white light filter 214a of the rotation filter 214 is positioned again in the optical path of the light source device 210 under the control of the controller 239. Accordingly, the white light is applied again by the light source device 210 to the observed region 100 after a predetermined time from application of the excitation light. Subsequently, under the control of the controller 239, the reflected light image acquiring unit 31 acquires the white light image Pw2 of the observed region 100 that is captured by the reflected light imaging unit 26 at timing T3 at which the white light from the light source device 210 is applied to the observed region 100, and transmits each video signal of the acquired white light image Pw2 after digital conversion to the pre-processor 33.

The timing T2 at which the excitation light is applied is timing between the timing T1 at which the white light from the light source device 210 is applied to the observed region 100 and the timing T3 at which the white light from the light source device 210 is applied again to the observed region 100. The fluorescent light image Pf of the observed region 100 that is captured at the timing T2 is image information after the white light image Pw1 of the observed region 100 at the timing T1, and the fluorescent light image Pf is image information older than that of the white light image Pw2 of the observed region 100 that is captured at the timing T3. In other words, the white light images Pw1 and Pw2 of the observed region 100 at the timing T1 and T3 are the chronologically continuous image information between which the fluorescent light image Pf of the observed region 100 at the timing T2 is.

Subsequently, the image processing device 230 performs the pre-processing on each video signal of the white light image Pw2 and the fluorescent light image Pf of the observed region 100, which are acquired at step S302 (step S303) as in the case of step S103 according to the first embodiment represented in FIG. 6. Thereafter, the image processing device 230 performs the variation detection process on the reflected light image of the observed region 100 (step S304). At step S304, the controller 239 controls the variation detector 235 such that it performs the variation detection process, representative vector calculation process, and filtering process on the white light image Pw2 to be processed on the basis of the chronologically continuous white light images Pw1 and Pw2 of the observed region 100 between which the fluorescent light image Pf of the observed region 100 is.

Under the control of the controller 239, the variation detector 235 detects the variation component of the white light image Pw2 to be processed on the basis of the white light image Pw2 to be processed, which is acquired from the pre-processor 33, and the old white light image Pw1, which is read from the storage unit 34. Specifically, the variation detector 235 divides the white light image Pw2 to be processed, which is m×n-pixel image information, to M×N pixel blocks. The variation detector 235 calculates a variation vector of each pixel block of the white light image Pw2 to be processed, for example, using the block matching method in which the white light image Pw2 consisting of M×N-pixel blocks is set as a reference image and the old white light image Pw1 that is read from the storage unit 34 is set as a reference image. The variation detector 235 calculates a variation component V(i,j) of variation vector of each pixel block of the white light image Pw2 to be processed from Equation (1). The variation detector 35 generates the variation component map that contains the variation component V(i,j) of each pixel block of the white light image Pw2. The variation component V(i,j) of each pixel block of the white light image Pw2 is a variation component at the timing T3 after the predetermined time from the timing T2 of the fluorescent light image Pf of the observed region 100. As in the case of the first embodiment, the variation detector 235 performs the process for comparing the luminance of the pixel of interest and that of the neighboring pixels with respect to each pixel of the white light image Pw2 to be processed, and performs the above-described filtering process on the basis of the result of the luminance comparison process.

The variation detector 235 detects, with respect to each pixel or each pixel block, the variation vector between the white light image Pw2 to be processed and the old white light image Pw1, and calculates the representative vector $V_r$ that represents the detected variation vectors. The variation detector 235 transmits the variation component map of the white light image Pw2 after the filtering process and the representative vector $V_r$ to the variation compensator 236.

Subsequently, the image processing device 230 performs the variation compensation process on the reflected light image of the observed region 100 (step S305). At step S305, the controller 239 controls the variation compensator 236 to compensate for the variation component of the white light image Pw2 to be processed, which variation component is detected by the variation detector 235, to the variation component at the same timing as that at which the fluorescent light image Pf to be processed is captured.

Under the control of the controller 239, the variation compensator 236 compensates for the variation component of the white light image Pw2 to be processed, i.e., the white light image Pw2 of the observed region 100 at the timing T3, to the variation component at the timing T2 same as that of fluorescent light image Pf of the observed region 100.

Specifically, the variation compensator 236 acquires the variation component map of the white light image Pw2 to be processed and the representative vector $V_r$ from the variation detector 235. The variation compensator 236 calculates the variation compensation vector $V_f$ on the basis of the acquired representative vector $V_r$ and time intervals ΔT1 and ΔT2 between the white light images Pw1 and Pw2 of the observed region 100 and the fluorescent light image Pf. The time interval ΔT1 is the lag between the timing T2 of the fluorescent light image Pf and the timing T1 of the old white light image Pw1, and the time interval ΔT2 is the lag between the timing T3 of the white light image Pw2 to be processed and the timing T2 of the fluorescent light image Pf to be processed (see FIG. 5). From the following Equation (5), the variation compensator 236 calculates a variation compensation vector $V_f$ that is vector information that represents the difference between each variation vector of the white light image Pw2 at the timing T3 and each variation vector of the white light image at the timing T2.

$$V_f = \frac{\Delta T2}{\Delta T1 + \Delta T2} \times V_r \quad (5)$$

On the basis of the variation component map of the white light image Pw2 at the timing T3 and the variation compensation vector $V_f$, the variation compensator 236 compensates for each variation component in the variation component map to the variation component at the timing T2 of the fluorescent light image Pf. In this case, the variation compensator 236 subtracts the variation compensation vector $V_f$ from the variation vector of each pixel block in the variation component map at the timing T3, and calculates the variation component of the variation vector of each pixel block after the subtraction process as the variation component V(i,j) after the variation compensation process. The variation component V(i,j) after the variation compensation process is the variation component of the white light image Pw2 to be processed at the timing T2, and is calculated as represented by Equation (1). The variation compensator 236 generates the variation component map that contains the variation component V(i,j) after the variation compensation processes as the variation component with respect to each pixel block, and transmits the generated variation component map as the variation component map after the variation compensation process to the correction processor 36.

Subsequently, the image processing device 230 performs the correction process based on the detected variation component of the reflected light image of the observed region 100 (step S306). At step S306, the controller 239 controls the correction processor 36 such that it corrects the luminance value of the white light image to be processed taking into account the variation component V(i,j) after the variation compensation process by the variation compensator 236.

Under the control of the controller 239, the correction processor 36 corrects the luminance value of each pixel of the white light image Pw2 to be processed that is acquired from the pre-processor 33. In this case, the correction processor 36 acquires the variation component map after the variation compensation process from the variation compensator 236 instead of acquiring the variation component map from the variation detector 35, and performs the process procedure from step S201 to step S205 represented in FIG. 7, using the variation component map after the variation compensation process and the white light image Pw2 to be processed, which is acquired from the pre-processor 33. Accordingly, the correction processor 36 calculates, with respect to each pixel, a corrected luminance value $W_d(x,y)$ that is obtained by taking the variation component $V_d(x,y)$ after the variation compensation process into account for the luminance value of the white light image Pw2 to be processed, and generates a normalization image Pr that has the calculated luminance value $W_d(x,y)$ of each pixel (see FIG. 15). The correction processor 36 transmits the corrected luminance value $W_d(x,y)$ of each pixel of the normalization image Pr to the normalization processor 37.

The variation component $V_d(x,y)$ after the variation compensation process is obtained by dividing, on a pixel basis, the variation component V(i,j) of the pixel block in the variation component map after the variation compensation process by the variation compensator 236. The variation component $V_d(x,y)$ is the variation component at pixel coordinates (x,y) of the two-axis orthogonal coordinate system that is set to the white light image Pw2 to be processed. The variation component $V_d(x,y)$ after the variation compensation process is a variation component of each pixel of the white light image Pw2 to be processed at the timing T2 same as that of the fluorescent light image Pf of the observed region 100, and is a value that varies depending on the imaging distance between the observed region 100, which is the object, and the reflected light imaging unit 26 as in the case of the first embodiment. The positions of the subject are almost the same between in the normalization image Pr that contains, with respect to each pixel, the corrected luminance value $W_d(x,y)$ for which the variation component $V_d(x,y)$ after the variation compensation process is taken into account and the fluorescent light image Pf of the observed region 100 at the timing T2. The normalization image Pr has the luminance distribution that accurately reflects the imaging distance between the observed region 100, which is the subject, and the reflected light imaging unit 26 regardless of whether there is a positive reflected light pixel.

Thereafter, the image processing device 230 performs the normalization process on the fluorescent light image Pf of the observed region 100 as in the case of steps S106 to S108 represented in FIG. 6 (step S307). The image processing device 230 performs the post-processing on the normalized fluorescent light image of the observed region 100 processed at step S307 (step S308), and then performs the process for outputting the normalized fluorescent light image of the observed region 100 after the post-processing (step S309). Thereafter, when a process completion operation, such as a predetermined off operation, is performed as in the case of step S109 represented in FIG. 6 (YES at step S310), the image processing device 230 completes the process. In contrast, when the process completion operation is not performed (NO at step S310), the image processing device 230 returns to step S302 and repeats the process procedure from step S302 and the following steps. In this case, the controller 239 performs the process procedure from step S302 to step S310 in order to appropriately control each constituent of the image processing device 230.

As explained above, in the second embodiment of the present invention, white light images and fluorescent light images of the observed region are alternately acquired at the predetermined interval. In addition, on the basis of the two frames of white light image that are acquired sequentially between which the fluorescent light image is, the variation component of the white light image to be processed, which is one of the two-frames of white light image, is detected. The detected variation component is compensated to the variation component at the timing at which the fluorescent light image is captured, and the luminance value of the white light image to be processed is corrected taking the variation component after the variation compensation process into account. Other aspects of the configuration are similar to those of the first embodiment. Thus, functions and effects similar to those of the first embodiment can be achieved. Furthermore, the white light that illuminates the observed region and the excitation light that causes generation of fluorescent light from the observed region can be alternately applied at different timing. Thus, it is not required to separate the wavelength band of white light from the wavelength bane of fluorescent light, and the excitation light that causes generation of fluorescent light of the desired wavelength band can be applied regardless whether it is in or out of the wavelength band of white light. This increases flexibility in selecting a wavelength band of fluorescent light and excitation light that are used for fluorescence observation, which allows easy fluorescence observation of the observed region.

In the first and second embodiments, the corrected luminance calculator 36d calculates the corrected luminance value of the reflected light image to be processed (for example, the white light image of the observed region 100) taking the variation component of each pixel contained in the variation component map or in the variation component after the variation compensation process. However, the correction of the luminance value by the corrected luminance calculator 36d is not limited to this. The corrected luminance calculator 36d determines whether the reflected light image to be processed contains a pixel that receives a positive reflected light, i.e., the positive reflected light pixel. When a positive reflected light pixel is contained, the corrected luminance value that corresponds to the positive reflected light pixel may be set larger compared to the case where a positive reflected light pixel is not contained. In other words, the corrected luminance calculator 36d may change weighing of the coefficient of corrected luminance value between a positive reflected light pixel and pixels other than the positive reflected light pixel in order to set larger the weighing of the corrected luminance value of positive reflected light pixel compared to the pixels other than the positive reflected light pixel.

The corrected luminance calculator 36d determines whether a positive reflected light pixel is contained in the reflected light image to be processed. When a positive reflected light pixel is contained, the corrected luminance calculator 36d may perform a clip process for replacing the luminance value of the positive reflected light pixel to a predetermined luminance value. Specifically, the corrected luminance calculator 36d compares the luminance value of each pixel of the reflected light image to the pre-set threshold. The corrected luminance calculator 36d determines that a pixel with a luminance value larger than the threshold is a positive reflected light pixel. The corrected luminance calculator 36d replaces the luminance value of the positive reflected light pixel with a pre-set luminance value. This reduces the difference in luminance value between the positive reflected light pixel and the pixels other than the positive reflected light pixel. As a result, each luminance value of the fluorescent light image can be corrected with high accuracy without influence of positive reflected light from the observed region.

The corrected luminance calculator 36d calculates the corrected luminance value $W_d(x,y)$ by performing the adding process on the luminance value $W(x,y)$ and variation component $V_d(x,y)$ of the white light image to be processed. Alternatively, the corrected luminance calculator 36d may calculate the corrected luminance value $W_d(x,y)$ by performing a multiplying process on the luminance $W(x,y)$ and variation component $V_d(x,y)$ of the white light image to be processed.

In the first and second embodiments, the corrected luminance calculator 36d divides M×N pixel blocks to the original pixel units, i.e., to m×n pixels, and calculates the variation component $V_d(x,y)$ of each pixel. Alternatively, the corrected luminance calculator 36d may calculate the variation component $V_d(x,y)$ of each pixel by a known extension process using bilinear interpolation or bicubic interpolation.

In the first and second embodiments, the normalization processor 37 calculates the luminance value $Q(x,y)$ of the fluorescent light image from Equation (2). The constant K of Equation (2) may be a constant that depends on the exposure time or gain of the imaging device at the time of image capturing or a value that is previously set by the user via the input device 40. When the corrected luminance value $W_d(x,y)$ is 0, the luminance value $Q(x,y)$ of the normalized fluorescent light image is set to 0 in Equation (2). Alternatively, when the corrected luminance value $W_d(x,y)$ is 0, the luminance value $Q(x,y)$ of the normalized fluorescent light image may be set to a pre-set luminance value and warning of error may be issued.

In the first and second embodiments, 16×16-pixel pixel block is represented as an example of a pixel block in the variation component map. Alternatively, each pixel block in the variation component map may be a square pixel block of 3×3 pixels or 4×4 pixels, or may be a rectangular pixel block of 7×5 pixels or 4×6 pixels.

In the first and second embodiments, the white light is applied as an example of illuminating light to the observed region. Alternatively, the illuminating light that is applied to the observed region may be light of a desired color component, such as red or green.

In the first and second embodiments, the normalized fluorescent light image of the observed region is displayed on the image output device 50. Alternatively, the image output device 50 may simultaneously display the white light image and the normalized fluorescent light image of the observed region. In addition, the image output device 50 is not limited to one that displays on its screen the fluorescent light image of the observed region. The image output device 50 may be a printer that prints the white light image or the fluorescent light image of the observed region on a printing medium, such as paper, or may be a storage device that includes a built-in storage medium, such as a hard disk, or a portable storage media, such as a memory card, and that stores the white light image or the fluorescent light image of the observed region in the storage media.

In the first and second embodiments, the endoscope that incorporates the imaging unit in the insertion unit that is connected to the image processing device is represented as an example of an image capturing apparatus according to the present invention. Alternatively, an image capturing apparatus in which the image processing device and the imaging unit according to the present invention may be configured separately may be used. In this case, the imaging unit stores raw data of video signals captured by the independent imaging unit in storage medium, such as a memory card, and stores accompanying information, such as imaging conditions or data obtained by image capturing in the storage medium as header information. The image processing device according to the present invention may read stored information, such as video signals, from the storage medium and the above-described various processes may be performed on the read video signals. The information, such as video signals captured by the imaging unit, may be acquired by the image processing device via the storage medium or may be acquired by the image processing device via a wired or wireless communication network.

In the first embodiment, the wavelength band of excitation light is set to 680 to 740 nm. Alternatively, any desired wavelength band of excitation light may be set as long as the excitation light causes generation of fluorescent light out of the wavelength band of illuminating light, such as white light that is applied to the observed region. In this case, the wavelength band of fluorescent light that is generated due to the excitation light may be a wavelength band of illuminating light, such as white light, or higher or lower.

In the second embodiment, the wavelength band of excitation light is set to 490 to 550 nm. Alternatively, the wavelength band of excitation light in the second embodiment may be in or out of the wavelength band of illuminating light, such as the white light that is applied to the observed region. In this case, the wavelength band of fluorescent light that is generated due to the excitation light may be in or out of the wavelength band of illuminating light, such as white light.

In the first and second embodiments, the endoscope for observing a subject, such as body tissue, is explained as an example of an image capturing apparatus that includes the image processing device according to the present invention. Alternatively, the image capturing apparatus according to the present invention may be an endoscope or a microscope that is used in fields other than the medical field, or may be an imaging device other than endoscopes or microscopic apparatuses, such as a digital camera or a digital video camera, or a portable information terminal device, such as a mobile phone with an imaging function. The image processing device according to the present invention is not limited to those incorporated in endoscopes or microscopes used in fields other than the medical field. Furthermore, the image processing device may be incorporated in an image capturing apparatus, such as a digital camera or a digital video camera, other than endoscopes or microscopes or may be incorporated in a portable information terminal device, such as a mobile phone with an imaging function.

In the first and second embodiments, the process procedure of the image processing device by software based on operations of the controller that executes the process programs is explained. Alternatively, the image processing device according to the present invention may perform a process procedure by hardware. In the computer readable storage medium of each embodiment, image processing programs that allow image processing along with the image processing method according to the embodiment are stored. The storage medium may be a built-in storage medium, such as a hard disk, or a portable storage medium, such as a memory card.

The image processing devices, the computer readable storage media, and the image processing methods according to the embodiments accurately correct the luminance of a fluorescent light image to be observed.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:
1. An image processing device, comprising:
a reflected light image acquiring unit that acquires a reflected light image of an observed region, the reflected light image being obtained from light reflected from the observed region;
a fluorescent light image acquiring unit that acquires a fluorescent light image of the observed region, the fluorescent light image being obtained from fluorescent light that is generated from the observed region by excitation light;
a variation detecting unit that detects a variation component of the reflected light image on the basis of an old reflected light image of the observed region and the reflected light image, the old reflected light image and the reflected light image being acquired by the reflected light image acquiring unit;
a correction process unit that performs a correction process on a luminance value of the reflected light image, taking the variation component into account; and
a normalization process unit that performs a normalization process on a luminance value of the fluorescent light image, using the luminance value of the reflected light image on which the correction process is performed by the correction process unit;
wherein the fluorescent light image is an image different from the reflected light image; and
wherein the correction process unit sets higher the corrected luminance value of the reflected light image with an increase in the variation component, and sets lower the corrected luminance value of the reflected light image with a decrease in the variation component.

2. The image processing device according to claim 1, wherein
the variation detecting unit divides the reflected light image into a plurality of pixel blocks, calculates a variation vector of each of the pixel blocks with reference to the old reflected light image, and calculates a variation component of each of the variation vectors of the pixel blocks as the variation component of the reflected light image.

3. The image processing device according to claim 1, wherein
the correction process unit calculates, with respect to each corresponding pixel between the reflected light image and the variation component, a corrected luminance value that is obtained by taking the variation component into account for the luminance value of the white light image, and
the normalization process unit performs the normalization process on the luminance value of the fluorescent light image, using the corrected luminance value that is calculated by the correction process unit.

4. The image processing device according to claim 3, wherein the correction process unit includes
a variation amount calculating unit that calculates a general variation amount of the reflected light image on the basis of the variation component of the reflected light image that is detected by the variation detecting unit;
a variation component storage unit that stores a variation component of the old reflected light image;
a replacement process unit that compares the general variation amount of the reflected light image, which is calculated by the variation amount calculating unit, to a predetermined threshold, outputs the variation component of the reflected light image when the general variation amount of the reflected light image is the predetermined threshold or higher, and replaces the variation component of the reflected light image with the variation component of the old reflected light image in the variation component storage unit and outputs the variation component of the old reflected light image when the general variation amount of the reflected light image is lower than the predetermined threshold; and
a corrected luminance calculating unit that calculates a corrected luminance value of the reflected light image for which the variation component that is output by the replacement process unit is taken into account,
wherein the normalization process unit performs the normalization process on the luminance value of the fluorescent light image using the corrected luminance value of the reflected light image that is calculated by the corrected luminance calculating unit.

5. The image processing device according to claim 4, wherein
the corrected luminance calculating unit sets higher the corrected luminance value of the reflected light image with an increase in the variation component that is output by the replacement process unit, and sets lower the corrected luminance value of the reflected light image with a decrease in the variation component that is output by the replacement process unit.

6. The image processing device according to claim 4, wherein the variation amount calculating unit calculates, as the general variation amount of the reflected light image, an average value of the variation components of the reflected light image.

7. The image processing device according to claim 1, wherein
when the luminance value of the reflected light image after the correction process is other than 0, the normalization process unit divides the luminance value of the fluorescent light image by the luminance value other than 0 with respect to each corresponding pixel between the reflected light image and the fluorescent light image, and
when the luminance value of the reflected light image after the correction process is 0, the normalization process unit sets to 0 the luminance value of the fluorescent light image corresponding to the luminance value that is 0.

8. The image processing device according to claim 1, further comprising
a variation compensating unit that compensates for the variation component of the reflected light image that is detected by the variation detecting unit, to a variation component at the same timing as that at which the fluorescent light image is captured,
wherein the correction process unit performs the correction process on the luminance value of the reflected light image taking the variation component that is compensated for by the variation compensating unit.

9. A non-transitory computer-readable storage medium that stores therein an image processing program that contains instructions for causing a computer to perform:
acquiring a reflected light image of an observed region and a fluorescent light image of the observed region, the reflected light image being obtained from light reflected from the observed region, and the fluorescent light image being obtained from fluorescent light that is generated by excitation light;
detecting a variation component of the reflected light image;
performing a correction process on a luminance value of the reflected light image taking the variation component into account; and
performing a normalization process on a luminance value of the fluorescent light image using the luminance value of the reflected light image after the correction process;
wherein the fluorescent light image is an image different from the reflected light image; and
wherein the correction process sets higher the corrected luminance value of the reflected light image with an increase in the variation component, and sets lower the corrected luminance value of the reflected light image with a decrease in the variation component.

10. An image processing method, comprising:
acquiring a reflected light image of an observed region and a fluorescent light image of the observed region, the reflected light image being obtained from light reflected from the observed region, and the fluorescent light image being obtained from fluorescent light that is generated by excitation light;
detecting a variation component of the reflected light image;
performing a correction process on a luminance value of the reflected light image taking the variation component into account; and
performing a normalization process on a luminance value of the fluorescent light image using the luminance value of the reflected light image after the correction process;
wherein the fluorescent light image is an image different from the reflected light image; and
wherein the correction process sets higher the corrected luminance value of the reflected light image with an increase in the variation component, and sets lower the corrected luminance value of the reflected light image with a decrease in the variation component.

* * * * *